US012579846B2

(12) United States Patent
Koda

(10) Patent No.: US 12,579,846 B2
(45) Date of Patent: Mar. 17, 2026

(54) INFORMATION PROCESSING APPARATUS, INFORMATION PROCESSING METHOD, AND NON-TRANSITORY RECORDING MEDIUM

(71) Applicant: NEC Corporation, Tokyo (JP)

(72) Inventor: Yoshinori Koda, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/851,354

(22) PCT Filed: May 10, 2023

(86) PCT No.: PCT/JP2023/017628
§ 371 (c)(1),
(2) Date: Sep. 26, 2024

(87) PCT Pub. No.: WO2023/228754
PCT Pub. Date: Nov. 30, 2023

(65) Prior Publication Data
US 2025/0218228 A1 Jul. 3, 2025

(30) Foreign Application Priority Data

May 25, 2022 (JP) ................................. 2022-085036

(51) Int. Cl.
*G06V 40/50* (2022.01)
*A61B 5/1171* (2016.01)
(Continued)

(52) U.S. Cl.
CPC ............ *G06V 40/50* (2022.01); *A61B 5/1172* (2013.01); *A61B 5/1176* (2013.01);
(Continued)

(58) Field of Classification Search
CPC ............... G06V 40/50; G06V 40/1359; G06V 40/1376; A61B 5/1172; A61B 5/1176; A61B 2503/045; G16H 10/60
See application file for complete search history.

(56) References Cited

U.S. PATENT DOCUMENTS 5,572,597 A 11/1996 Chang et al.
2001/0048756 A1 12/2001 Staub et al.
(Continued)

FOREIGN PATENT DOCUMENTS

JP 2001-076072 A 3/2001
JP 2004039909 A * 2/2004
(Continued)

OTHER PUBLICATIONS

International Search Report for PCT Application No. PCT/JP2023/017628, mailed on Jul. 25, 2023.

*Primary Examiner* — Premal R Patel
(74) *Attorney, Agent, or Firm* — Sughrue Mion, PLLC

(57) ABSTRACT

An information processing apparatus (1) comprises: a storage unit (11) that stores first identification information for indicating a person related to a newborn; a first newborn information acquisition unit (12) that acquires first newborn living-body information from the newborn; a first determination unit (13) that determines which one of predetermined plurality types of pattern is a type of pattern that the first newborn living-body information has; and a storage control unit (14) that causes the storage unit (11) to store first determination information indicating a determination result by the first determination unit (13) in association with the first identification information.

10 Claims, 12 Drawing Sheets

(51) Int. Cl.
    *A61B 5/1172*         (2016.01)
    *G06V 40/12*          (2022.01)
    *G16H 10/60*          (2018.01)
(52) U.S. Cl.
    CPC ...... *G06V 40/1359* (2022.01); *G06V 40/1376*
        (2022.01); *G16H 10/60* (2018.01); *A61B*
                         *2503/045* (2013.01)

(56)               References Cited

U.S. PATENT DOCUMENTS

2008/0101662 A1*   5/2008   Lo ...................... G06V 40/1365
                                          382/124
2023/0214469 A1     7/2023   Hayashi et al.

FOREIGN PATENT DOCUMENTS

JP      2005-176962 A     7/2005
JP      2008-108104 A     5/2008
JP      2008-113754 A     5/2008
JP      2019-200688 A    11/2019
WO    2021/250839 A1   12/2021

* cited by examiner

FIG. 12A

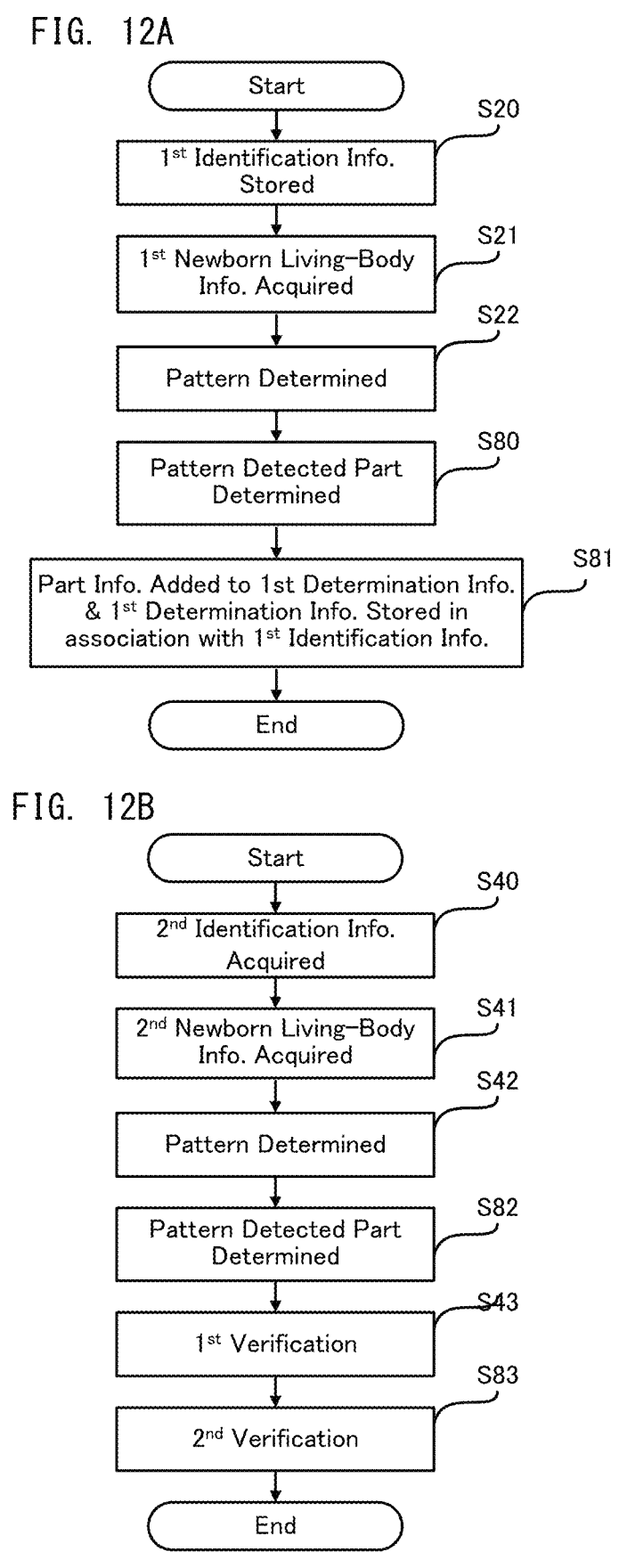

Start

1st Identification Info. Stored — S20

1st Newborn Living-Body Info. Acquired — S21

Pattern Determined — S22

Pattern Detected Part Determined — S80

Part Info. Added to 1st Determination Info. & 1st Determination Info. Stored in association with 1st Identification Info. — S81

End

FIG. 12B

Start

2nd Identification Info. Acquired — S40

2nd Newborn Living-Body Info. Acquired — S41

Pattern Determined — S42

Pattern Detected Part Determined — S82

1st Verification — S43

2nd Verification — S83

End

Start

1st Identification Info. Stored — S20

1st Newborn Living-Body Info. Acquired — S21

Pattern Determined — S22

High Accuracy? — S90

No

Yes

Feature Amount Extracted — S91

Feature-Amount Extracted Part Determined — S92

Feature Amount and Part Info. Added to 1st Determination Info. — S93

1st Determination Info. Stored in association with 1st Identification Info. — S23

End

F

| (1) | (2) | (3) |
| (4) | (5) | (6) |
| (7) | (8) | (9) |

INFORMATION PROCESSING APPARATUS, INFORMATION PROCESSING METHOD, AND NON-TRANSITORY RECORDING MEDIUM

This application is a National Stage Entry of PCT/JP2023/017628 filed on May 10, 2023, which claims priority from Japanese Patent Application 2022-085036 filed on May 25, 2022, the contents of all of which are incorporated herein by reference, in their entirety.

TECHNICAL FIELD

This disclosure relates to technical fields of an information processing apparatus, information processing method, and recording medium.

BACKGROUND ART

There is disclosed in Patent Document 1 a technique for avoiding the occurrence of a mistake caused by an artificial error when authentication of an authentication person is implemented, by reading a vein pattern of a body portion with respect to each of a plurality of persons, generating pattern data for authentication representing a plurality of vein patterns read, registering the pattern data for authentication on a predetermined registration place, reading the vein pattern of the portion with respect to the authentication person, and verifying the vein pattern read with the vein pattern included in the registered pattern data for authentication. There is disclosed in Patent Document 2 a technique for imaging a subject, such as fingertip, without a blur, by providing a photo sensor for converting light and dark by unevenness of a fingertip into an electric signal in order to obtain a fingerprint image of a fingertip, the photo sensor being configured by a plurality of DG-TFTs arranged in a matrix, where a light diffusing film for diffusing light is formed on a surface, for an image with strong contrast. There is disclosed in Patent Document 3 a technique for ensuring an individual confirmation for patients, newborns, and the like at medical organizations such as hospitals and the like, by registering in advance living body characteristics, such as the iris, of a subject to be registered, such as a new patient, a newborn, and the like; obtaining at the moment of verification for a re-examination or the like, the living body characteristics of an individual to be verified; and providing an individual confirmation unit that executes individual confirmation for a person to be verified by comparing the living body characteristics of the individual to be verified to the living body characteristics registered, for eliminating a patent or baby mix-up and also eliminating impersonation by another person.

CITATION LIST

Patent Document

[Patent Document 1] JP 2008-108104 A
[Patent Document 2] JP 2004-039909 A
[Patent Document 3] JP 2001-076072 A

SUMMARY

Technical Problem

The object of this disclosure is to provide an information processing apparatus, information processing method, and recording medium for improving techniques described in the Citation List.

Solution to Problem

One aspect of an information processing apparatus comprises: a storage unit that is configured to store first identification information for indicating a person related to a newborn; a first newborn information acquisition unit that is configured to acquire first newborn living-body information from the newborn; a first determination unit that is configured to determine which one of predetermined plurality types of pattern is a type of pattern that the first newborn living-body information has; and a storage control unit that is configured to cause the storage unit to store first determination information indicating a determination result by the first determination unit in association with the first identification information.

One aspect of the information processing method comprises: storing first identification information for indicating a person related to a newborn in a storage unit; acquiring first newborn living-body information from the newborn; determining which one of predetermined plurality types of pattern is a type of pattern that the first newborn living-body information has; and causing the storage unit to store first determination information indicating a determination result in association with the first identification information.

One aspect of a recording medium on which a computer program that allows a computer to execute an information processing method is recorded, the information processing method comprising: storing first identification information for indicating a person related to a newborn in a storage unit; acquiring first newborn living-body information from the newborn; determining which one of predetermined plurality types of pattern is a type of pattern that the first newborn living-body information has; and causing the storage unit to store first determination information indicating a determination result in association with the first identification information.

BRIEF DESCRIPTION OF DRAWINGS

FIG. 12A includes flow charts, each illustrating a flow of an information processing operation performed by the information processing apparatus according to the eighth example embodiment.

FIG. 12B includes flow charts, each illustrating a flow of an information processing operation performed by the information processing apparatus according to the eighth example embodiment.

DESCRIPTION OF EXAMPLE EMBODIMENTS

Figure 1:
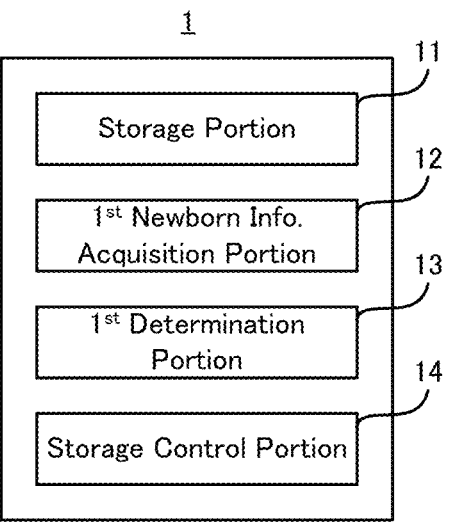
FIG. 1 is a block diagram illustrating a configuration of an information processing apparatus according to a first example embodiment.

There will be described below example embodiments referring to the drawings, with respect to an information processing apparatus, information processing method, and recording medium.

1: First Example Embodiment

A first example embodiment of an information processing apparatus, information processing method, and recording medium will be described. Hereinafter, there will be described the first embodiment of the information processing apparatus, information processing method, and recording medium, using an information processing apparatus 1 to which the first example embodiment of the information processing apparatus, information processing method, and recording medium is applied.

[1-1: Configuration of Information Processing Apparatus 1]

Referring to FIG. 1, a configuration of the information processing apparatus 1 according to the first example embodiment will be described. FIG. 1 is a block diagram illustrating the configuration of the information processing apparatus 1 according to the first example embodiment.

As shown in FIG. 1, the information processing apparatus 1 comprises a storage portion 11, a first newborn information acquisition portion 12, a first determination portion 13, and a storage control portion 14. The storage portion 11 stores a first identification information for identifying a person related to a newborn. The first newborn information acquisition portion 12 acquires first newborn living-body information from the newborn. The first determination portion 13 determines which one of a predetermined plurality of types of patterns is the one that the first newborn living-body information has. The storage control portion 14 causes the storage portion 11 to store first determination information indicating the determination result by the first determination portion 13, in in association with the first identification information.

[1-2: Technical Effectiveness of Information Processing Apparatus 1]

The information processing apparatus 1 according to the first example embodiment causes the storage portion 11 to store in association with the first identification information, the first determination information indicating which one of the predetermined plurality of types of patterns is the one that the first newborn living-body information has. Thereby, it is possible to identify newborns with high accuracy.

2: Second Example Embodiment

A second example embodiment of an information processing apparatus, information processing method, and recording medium will be described. Hereinafter, there will be described the second example embodiment of the information processing apparatus, information processing method, and recording medium, using an information processing apparatus 2 to which the second example embodiment of the information processing apparatus, information processing method, and recording medium is applied.

[2-1: Configuration of Information Processing Apparatus 2]

Figure 2:
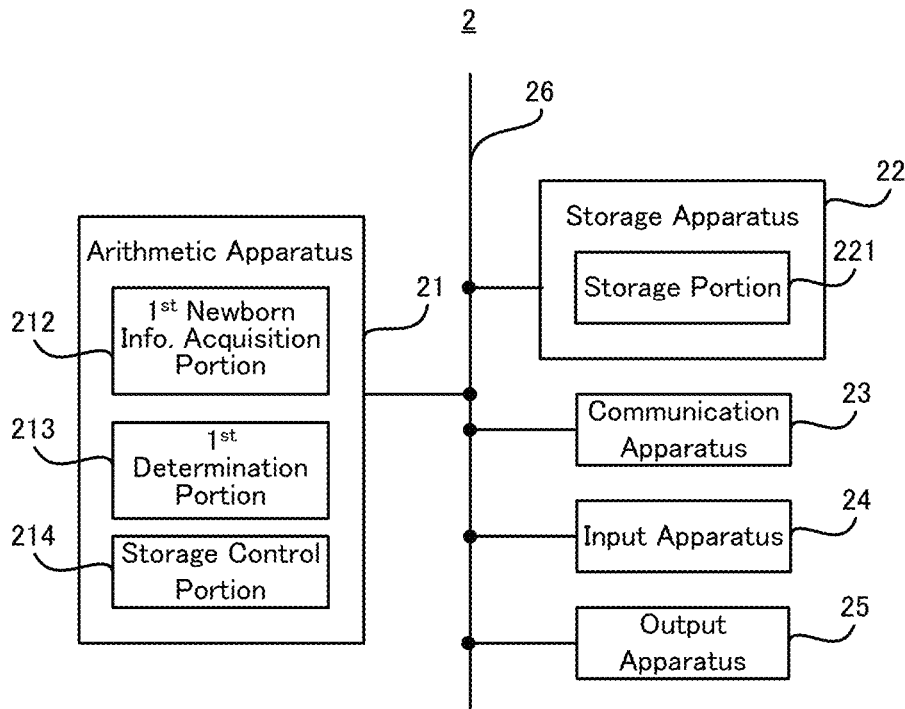
FIG. 2 is a block diagram illustrating a configuration of an information processing apparatus according to a second example embodiment.

Referring to FIG. 2, a configuration of the information processing apparatus 2 according to the second example embodiment will be described. FIG. 2 is a block diagram illustrating the configuration of the information processing apparatus 2 according to the second example embodiment.

As shown in FIG. 2, the information processing apparatus 2 comprises an arithmetic apparatus 21 and a storage apparatus 22. Furthermore, the information processing apparatus 2 may comprise a communication apparatus 23, an input apparatus 24, and an output apparatus 25. However, the information processing apparatus 2 may not comprise at least one of the communication apparatus 23, the input apparatus 24, and the output apparatus 25. The arithmetic apparatus 21, the storage apparatus 22, the communication apparatus 23, the input apparatus 24, and the output apparatus 25 may be connected through the data bus 26.

The arithmetic apparatus 21 includes at least one of, for example, CPU (Central Processing Unit), GPU (Graphics Processing Unit), and FPGA (Field Programmable Gate Array). The arithmetic apparatus 21 reads a computer program. For example, the arithmetic apparatus 21 may read a computer program stored in the storage apparatus 22. For example, the arithmetic apparatus 21 may read a computer program stored in a computer-readable and non-transient recording medium, using a recording-medium read apparatus, not shown, provided by the information processing apparatus 2 (e.g., the input apparatus 24, which will be described later). The arithmetic apparatus 21 may acquire (i.e., download or read) a computer program from an apparatus, not shown, disposed outside the information processing apparatus 2 via the communication apparatus 23 (or another communication apparatus). The arithmetic apparatus 21 executes the computer program loaded. Consequently, in the arithmetic apparatus 21, logical function blocks for executing operations to be performed by the information processing apparatus 2 are realized. In other words, the arithmetic apparatus 21 can function as a controller for realizing the logical function blocks for executing operations (in other words, processing) to be performed by the information processing apparatus 2.

FIG. 2 shows an example of the logical functional blocks realized in the arithmetic apparatus 21 for executing an information processing operation. As shown in FIG. 2, there are realized in the arithmetic apparatus 21: a first newborn information acquisition portion 212 that is a specific example of "a first newborn information acquisition unit" described in supplementary notes to be described later; a first determination portion 213 that is a specific example of "a first determination unit" described in the supplementary notes to be described later; and a storage control portion 214 that is a specific example of "a storage control unit" described in the supplementary notes to be described later. Operation of each of the first newborn information acquisition portion 212, the first determination portion 213, and the storage control portion 214 will be described later referring to FIG. 3.

The storage apparatus 22 is capable of storing desired data. For example, the storage apparatus 22 may temporarily store computer programs executed by the arithmetic apparatus 21. The storage apparatus 22 may temporarily store data that is temporarily used by the arithmetic apparatus 21 when the arithmetic apparatus 21 is running a computer program. The storage apparatus 22 may store data that the information processing apparatus 2 stores for long periods. The storage apparatus 22 may include at least one of a RAM (Random Access Memory), ROM (Read Only Memory, hard disk apparatus, magneto-optical disk apparatus, and SSD (Solid State Drive). That is, the storage apparatus 22 may include a non-transient recording medium. In the storage apparatus 22, a storage portion 221 may be realized, the storage portion 221 being a specific example of "a storage unit" described in the supplementary notes to be described later. However, the storage portion 221 which is a specific example of "a storage unit" may be realized in a storage system other than the storage apparatus 22

The communication apparatus 23 can communicate with an apparatus external to the information processing apparatus 2 through a communication network (not shown). The communication apparatus 23 may be a communication interface configured based on communication standards, such as Ethernet (registered trademark), Wi-Fi (registered trademark), Bluetooth (registered trademark), USB (Universal Serial Bus), and the like.

The input apparatus 24 is an apparatus that receives input of information to the information processing apparatus 2 from the outside of the information processing apparatus 2. For example, the input apparatus 24 may include an operation apparatus (for example, at least one of a keyboard, mouse track ball, touch panel, pointing device for pen tablets and the like, button) operable by an operator of the information processing apparatus 2. For example, the input apparatus 24 may include a read apparatus that can read information recorded as data in a recording medium which is externally attachable to the information processing apparatus 2.

The output apparatus 25 is an apparatus that outputs information to the outside of the information processing apparatus 2. For example, the output apparatus 25 may output the information as an image. In other words, the output apparatus 25 may include a display apparatus (so-called a display) that is capable of displaying an image showing information to be output. As examples of the display apparatus, there are a liquid crystal display, OLED (Organic Light Emitting Diode) display, and the like). For example, the output apparatus 25 may output information as sound. That is, the output apparatus 25 may include an audio apparatus (so-called a speaker) capable of outputting audio. For example, the output apparatus 25 may output information on a paper. In other words, the output apparatus 25 may include a print apparatus (so-called a printer) that can print desired information on a paper. Further, the input apparatus 24 and the output apparatus 25 may be integrally formed as a touch panel.

The hardware configuration shown in FIG. 2 is an example. Another apparatus other than apparatuses shown in FIG. 2 may be added. A part of the apparatuses shown in FIG. 2 may not be provided. In addition, a part of the apparatuses may be substituted for another apparatus having a similar function. In addition, a part of the functions of the second example embodiment may be provided by another apparatus through a network. The functions of the second example embodiment may be distributed to a plurality of apparatuses to be realized. Thus, the hardware configuration shown in FIG. 2 can be changed as appropriate.

[2-2: Information Processing Operation Performed by Information Processing Apparatus 2]

Figure 3:
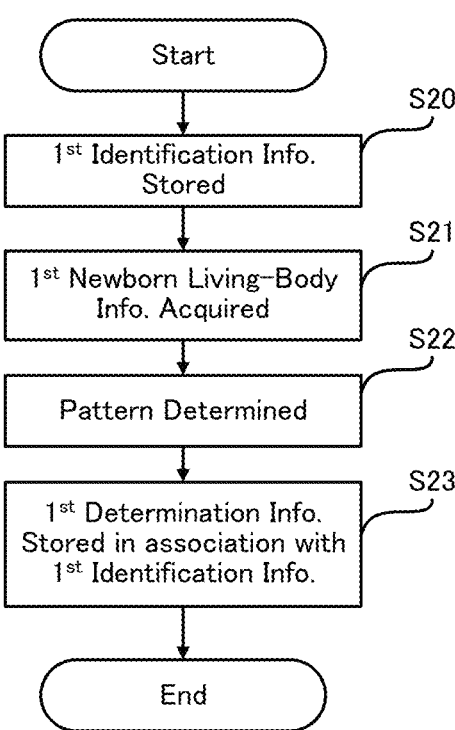
FIG. 3 is a flow chart illustrating a flow of an information processing operation performed by the information processing apparatus according to the second example embodiment.

Referring to FIG. 3, a flow of an information processing operation performed by the information processing apparatus 2 according to the second example embodiment will be described.

FIG. 3 is a flow chart illustrating a flow of the information processing operation performed by the information processing apparatus 2 according to the second example embodiment. As shown in FIG. 3, the storage portion 221 stores the first identification information for identifying a person related to a newborn (step S20).

The first newborn information acquisition portion 212 acquires the first newborn living-body information from the newborn (step S21). The first newborn information acquisition portion 212 may acquire more than one piece of the first newborn living-body information from the newborn.

The first determination portion 213 determines which one of the predetermined plurality of types of pattern is the one that the first newborn living-body information has (step S22). The first determination portion 213 may determine which one of the predetermined plurality of types of pattern is the one that the first newborn living-body information has, with respect to each of a plurality of pieces of the first newborn living-body information. The specific example of the pattern that the first newborn living-body information has will be described in detail in other example embodiments mentioned below.

The storage control portion 214 causes the storage portion 221 to store first determination information indicating the determination result by the first determination portion 213 in association with the first identification information (step S23). The storage control portion 214 may causes the storage portion 211 to store the first determination information in association with the first identification information, the first determination information being obtained by combining the determination results by the first determination portion 213, each of the determination results corresponding to each of the plurality of pieces of the first newborn living-body information. The first determination information may be information indicating an array of element information indicating the determination result of the pattern (hereinafter, sometimes referred to as "sequence data").

The operation on step S20 may not be continuous with the operations from step S21 to step S23. That is, the operation on step S20 may be performed in advance.

The present example embodiment may be applied in a scene where the delivery is performed in a place other than home such as a hospital. Especially, the present example embodiment may be applied before the newborn moves to home from a place other than home. The person related to the newborn may be a pre-registered person, and at least may be a person who is being together when the newborn moves from a place other than home to home. The person related to the newborn may be, for example, a person who is being together with the newborn when the newborn is released from hospital which is a place of birth.

The operations from step S21 to step S23 may be operations to be performed at the moment when it is possible to surely specify who the newborn is from and also before the newborn moves from a place other than home to home.

[2-3: Technical Effectiveness of Information Processing Apparatus 2]

Since the surface of a newborn is often covered with oil, sheep water, etc., it is often difficult to obtain living-body information that enables accurate identification of the newborn. In particular, it is often difficult to acquire living-body information that enables accurate identification of the newborn, in a case that the delivery takes place under conditions that the postpartum care is likely to be insufficient such as inadequate medical facilities or the like.

The information processing apparatus 2 according to the second example embodiment causes the storage portion 221 to store the first determination information in association with the first identification information, the first determination information indicating which one of the predetermined plurality of types of pattern is the one that the first newborn living-body information has. Thereby, it is possible to perform identification of the newborn with high accuracy. Since the information processing apparatus 2 uses the identification information of the person related to the newborn and the first determination information of the newborn, it is possible to perform identification of the newborn with high accuracy even when, for example, living-body information having a constant quality or higher, which is the level to be required by biometric authentication for an adult, cannot be acquired. In particular, when the first determination information is the sequence data, the information processing apparatus 2 can perform identification of the newborn more accurately. The information processing apparatus 2 can accurately perform the identification of newborns even in a case that it is more difficult to acquire the living-body information of a constant quality or higher, because of early birth or the like.

3: Third Example Embodiment

A third example embodiment of an information processing apparatus, information processing method, and recording medium will be described. Hereinafter, there will be described the third example embodiment of the information processing apparatus, information processing method, and recording medium, using an information processing apparatus 3 to which the third example embodiment of the information processing apparatus, information processing method, and recording medium is applied.

The information processing apparatus 3 according to the third example embodiment differs from the information processing apparatus 2 according to the second example embodiment in that the first newborn living-body information is a fingerprint image. The other features of the information processing apparatus 3 may be the same as those of the information processing apparatus 2. For this reason, different parts from the example embodiments described above will be described in detail below, and with respect to other overlapping parts, the descriptions thereof will be omitted as appropriate.

[3-1: Fingerprint Pattern]

The Fingerprint of each finger of a human, including a newborn, can be classified into eight types of fingerprint patterns, for example: P-arch (Plain Arch: PA); T-arch (Tented Arch: TA); U-loop (Ulnar Loop: UL); R-loop (Radial Loop: RL); D-loop (Double Loop: DL); P-whorl (Plain Whorl: PW); C-whorl (Central Pocket Loop Whorl: CW); and A-whorl (Accidental Whorl: AW). The fingerprint pattern may represent an overall pattern of the fingerprint.

The P-arch (PA) may be a fingerprint in which the ridge starts at one side of the finger head and runs to the other side in an arcuate shape, and nothing flows back at all.

The T-arch (TA) may be a fingerprint in which: the ridge starts at one side of the finger head, and runs to the other side in an arcuate shape; nothing flows back at all; and the central portion has a spike.

U-loop (UL) may be a fingerprint that is formed by the hoof lines whose pattern flows from a pinky finger and has the deltas only on the other side of that flow. The hoof line in the U-loop may be a ridge that starts from the pinky finger side of the finger head, draws a horseshoe shape and returns to the original side.

The R-loop (RL) may be a fingerprint that is formed by the hoof lines whose pattern flows from a thumb and has the deltas only on the other side of that flow. The hoof line in the R-loop may be a ridge that starts from the thumb side of the finger head, draws a horseshoe shape and returns to the original side.

The D-loop (DL) may be a fingerprint that has two cores, each core including an independent shoulder, an independent delta, and at least one roof constituting a complete perimeter.

The P-whorl (PW) may be a fingerprint where the ridge of the whorl forms a single complete perimeter including two deltas, and whose shape is a circular shape or spiral shape.

The C-whorl (CW) may be a fingerprint where the ridge of the whorl forms a single compete perimeter, and whose shape is a circular shape such as a shape of an ellipse, a spiral shape, or a shape obtained by deforming a circle arbitrarily.

The A-whorl (AW) may be a fingerprint where the whorl does not conform to the rules of whorls and who includes two or more deltas.

[3-2: Information Processing Operation Using Information Processing Apparatus 3]

In the third example embodiment, the first newborn information acquisition portion 212 may obtain a plurality of fingerprint images from the newborn. The fingerprint images can be used as stable living-body information that can be obtained from a newborn. The stable living-body information may refer to living-body information that is less likely to change accompanying growth and can be used for individual identification. The pitch of the fingerprint of a newborn is very fine compared with an adult. For this reason, the first newborn information acquisition portion 212 may acquire a high-resolution fingerprint image. The first newborn information acquisition portion 212 may, for example, obtain the fingerprint images from the respective four fingers, that is, the thumbs and the forefingers of both hands.

In the third example embodiment, the first determination portion 213 may determine, for each of the fingerprint images, which one of plurality of types of fingerprint pattern is the one that the fingerprint image has. The first determination portion 213 may determine, for each of the fingerprint images, which one of the above 8 types of fingerprint pattern is the one that the fingerprint image has.

The first determination portion 213 may determine, for each of the fingerprint images, which one of 9 types of fingerprint pattern is the one that the fingerprint image has, the 9 types of fingerprint pattern being obtained by adding a type that the fingerprint pattern is unknown (unknown: UK) to the above 8 types of fingerprint pattern.

The first determination portion 213 may determine the respective P arch (Plain Arch: PA) and T arch (Tented Arch: TA) as Arch (Arch: A). Further, the first determination portion 213 may determine the respective P-whorl (Plain Whorl: PW), C-whorl (Central Pocket Loop Whorl: CW), and A-whorl (Accidental Whorl: AW) as Whorl (Worl: W). That is, the first determination portion 213 may determine which one of 6 types of fingerprint pattern where the unknown type is added to the Arch (A), the U-loop (Ulnar Loop: UL), the R-loop (Radial Loop: RL), the D-loop (Double Loop: DL), and the Whorl (W) is the one. The first determining portion 213 may determine which one of the above mentioned 6 types (or, 9 types or 8 types) of fingerprint pattern is the one that the fingerprint pattern has, for each of the four fingers, that is, the thumbs and forefingers of both hands.

The first determination portion 213 may determine which one of the above mentioned 6 types (or, 9 types or 8 types) of fingerprint pattern respectively is the one, by an algorithm. The first determination portion 213 may determine which one of the above mentioned 6 types (or, 9 types or 8 types) of fingerprint pattern respectively is the one, by deep learning. According to fingerprint image categorization, it is possible to improve the accuracy of identification. The first determining portion 213 may classify the fingerprint into maximal 9 types of fingerprint patterns in order to further improve the accuracy of identification.

In the third example embodiment, the storage control portion 214 may causes the storage portion 221 to store in association with the first identification information, the first determination information where the determination results by the first determination portion 213 corresponding to the plurality of fingerprint images respectively are combined with each other. For example, the storage control portion 214 may causes the storage portion 221 to store in association with the first identification information, the sequence data where the determination results corresponding to the fingerprint images of the four fingers respectively are combined with each other. When the first determination portion 213 determines the fingerprint pattern of each of the four fingers, the sequence data may be represented in such a way: for example, (left forefinger-left thumb-right thumb-right forefinger: Whorl (W)—Whorl (W)—Whorl (W)—Worl (W)).

For example, with respect to Japanese fingerprints, the appearance ratio of fingerprint patterns is said to be 50% for spiral (W), that is, the largest appearance ratio. Also, the appearance ratio of R loop (RL) or U loop (UL) is said to be 40%. Therefore, in a case that the fingerprint pattern of all fingerprints of the four fingers is Whorl (W) (left forefinger-left thumb-right thumb-right forefinger: W-W-W-W), the appearance ratio of this sequence data is 6.25% (4th power of 0.5). Also, in a case that the fingerprint pattern of the fingerprints of all left and right fingers (ten fingers) is Whorl (W) (W-W-W-W-W-W-W-W-W-W), the appearance ratio of this sequence data is 0.097% (10th power of 0.5), and the appearance ratio decreases compared with the case of four fingers.

The storage control portion 214 may add a reliability score in the first determination information. For example, the storage control portion 214 may add the reliability score according to the appearance ratio of the sequence data. For example, the storage control portion 214 may add a higher reliability score as the appearance ratio of the sequence data is lower. The reliability score may be used, for example, when verification using the first determination information is performed.

Further, when the first determination portion 213 determines that the fingerprint pattern of any one of the fingers is the unknown type (UK), the storage control portion 214 may reduce the reliability score. For example, the storage control portion 214 may reduce the reliability score according to the ratio of the number of fingers whose fingerprint is determined by the first determination portion 213 as the unknown type (UK) to all fingers. For example, in a case that the first determination portion 213 determines the fingerprint pattern for each of the four finger, when it is determined that the fingerprint of one finger of them is the unknown type (UK), the storage control portion 214 may reduce the reliability score by 25%. In addition, in a case that the first determination portion 213 determines the fingerprint pattern for each of the four fingers, when it is determined that the fingerprint patterns of two fingers of them are the unknown type (UK), the storage control portion 214 may reduce the reliability score by 50%. In addition, in a case that the first determination portion 213 determines the fingerprint pattern for each of the ten fingers, when it is determined that the fingerprint pattern of one finger is the unknown type (UK), the storage control portion 214 may reduce the reliability score by 10%. In addition, in a case that the first determination portion 213 determines the fingerprint pattern for each of the ten fingers, when it is determined that the fingerprint patterns of the two fingers of them are the unknown type (UK), the storage control portion 214 may reduce the reliability score by 20%.

The information processing apparatus 3 may determine the number of fingers for acquiring the fingerprint image, according to the accuracy to be required to the first determination information and the burden to the newborn. With respect to a newborn, all fingerprints are often registered after growth. Therefore, it is preferable to acquire all fingerprints from a newborn as well. However, this is a burden for newborns.

For example, the information processing apparatus 3 may determine to decrease the accuracy to be required to the first determination information when the estimated number of deliveries is large. In this instance, the information processing apparatus 3 may determine to acquire the fingerprints from the four fingers. In addition, the information processing apparatus 3 may determine to increase the accuracy to be required to the first determination information when the estimated number of deliveries is small. In this instance, for example, the information processing apparatus 3 may determine to acquire the fingerprints from ten fingers. For example, the output apparatus 25 may output as an image, information on the accuracy to be required to the first determination information. Further, for example, the output apparatus 25 may output as a sound, information on the accuracy to be required to the first determination information The above-mentioned 8 types of fingerprint pattern are only one example. Fingerprints may be classified into more than 8 types, for example, twenty or more types of patterns. For example, a user may specify the number of classified fingerprints according to the usage requirement of the information on the newborn. In this case, the first determining portion 213 may determine which one of the types of fingerprint pattern is the one, the types of fingerprint pattern corresponding to the number of classified fingerprints specified by the user.

[3-3: Technical Effectiveness of Information Processing Apparatus 3]

Since the body surface of a newborn is often covered with sebum, sheep water, etc., it is often difficult to acquire a fingerprint image that enables accurate identification for the newborn himself/herself. In particular, in a case that the delivery is performed in a situation that the care after birth is likely to be insufficient, such as insufficient medical facilities or the like, it is often difficult to acquire the finger print which enables high accuracy of the identification of the newborn.

In the third example embodiment, the information processing apparatus 3 causes the storage portion 221 to store the first determination information in association with the first identification information, the first determination information indicating which one of the predetermined plurality of types of fingerprint pattern is the fingerprint pattern of the fingerprint image. Therefore, it is possible to accurately perform the identification of newborns. The information processing apparatus 3 uses the identification information of the person related to a newborn and the fingerprint of the newborn. Therefore, it is possible to perform the identification of newborns with high accuracy it is possible to perform identification of the newborn with high accuracy even when the fingerprint image having a constant quality or higher, which is, for example, the level to be required in fingerprint authentication for an adult, cannot be acquired. In particular, when the first determination information is the sequence data based on the fingerprint patterns, the information processing apparatus 3 can perform identification for newborns with better accuracy.

4: Fourth Example Embodiment

A fourth example embodiment of an information processing apparatus, information processing method, and recording medium will be described. Hereinafter, there will be described the fourth example embodiment of the information processing apparatus, information processing method, and recording medium, using an information processing apparatus 4 to which the fourth example embodiment of the information processing apparatus, information processing method, and recording medium is applied.

[4-1: Configuration of Information Processing Apparatus 4]

Figure 4:
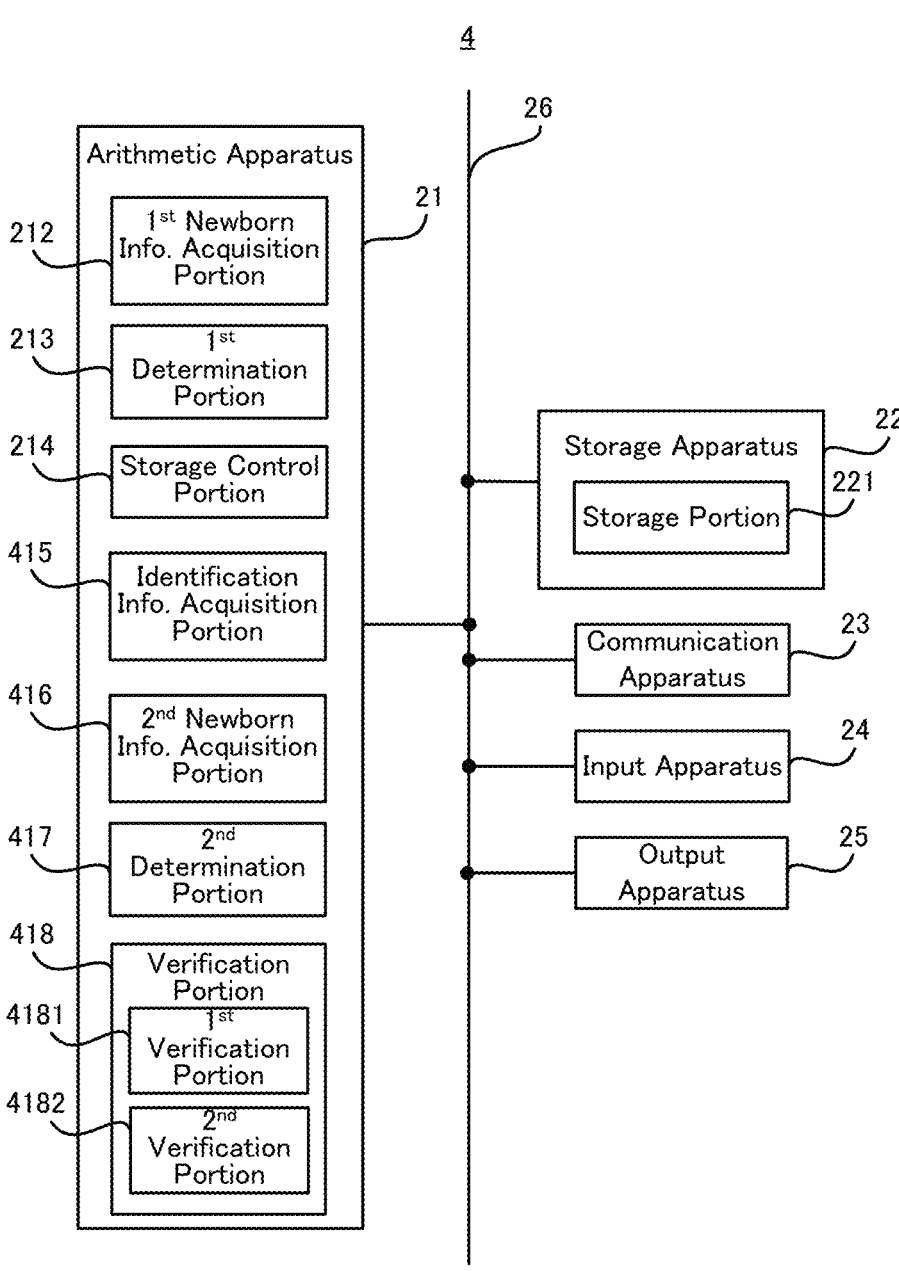
FIG. 4 is a block diagram illustrating a configuration of an information processing apparatus according to a fourth example embodiment.

Referring to FIG. 4, the configuration of the information processing apparatus 4 according to the fourth example embodiment will be described. FIG. 4 is a block diagram illustrating the configuration of the information processing apparatus 4 according to the fourth example embodiment.

As shown in FIG. 4, the information processing apparatus 4 according to the fourth example embodiment comprises the arithmetic apparatus 21 and the storage apparatus 22 similarly to the information processing apparatus 2 according to the second example embodiment or the information processing apparatus 3 according to the third example embodiment. Furthermore, the information processing apparatus 4 may comprise the communication apparatus 23, the input apparatus 24, and the output apparatus 25, similarly to the information processing apparatus 2 in the second example embodiment or the information processing apparatus 3 in the third example embodiment. However, the information processing apparatus 4 may not comprise at least one of the communication apparatus 23, the input apparatus 24, and the output apparatus 25. The information processing apparatus 4 according to the fourth example embodiment differs from the information processing apparatus 2 according to the second example embodiment or the information processing apparatus 3 according to the third example embodiment, in that the arithmetic apparatus 21 further comprises an identification information acquisition portion 415, a second newborn information acquisition portion 416, a second determination portion 417, and a verification portion 418. The verification portion 418 includes a first verification portion 4181 and a second verification portion 4182. The other features of the information processing apparatus 4 may be the same as those of the information processing apparatus 2 according to the second example embodiment or the information processing apparatus 3 according to the third example embodiment. For this reason, different parts from the respective example embodiments already described, will be described in detail below, and with respect to other overlapping parts, the descriptions thereof will be omitted as appropriate.

[4-2: Information Processing Operation Using Information Processing Apparatus 4]

Figure 5:
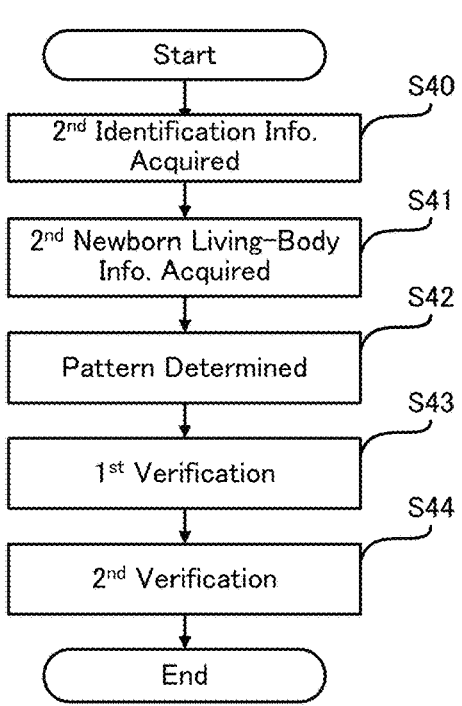
FIG. 5 is a flow chart illustrating a flow of an information processing operation performed by the information processing apparatus according to the fourth example embodiment.

Referring to FIG. 5, a flow of an information processing operation performed by the information processing apparatus 4 according to the fourth example embodiment will be described. FIG. 5 is a flow chart illustrating the flow of the information operation performed by the information processing apparatus 4 according to the fourth example embodiment. The information processing operation by the information processing apparatus 4 may be performed at a timing when the newborn moves to his/her home from a place other than his/her home, such as hospital. The information processing operation by the information processing apparatus 4 may be performed at the timing when the newborn leaves the hospital or the like.

As shown in FIG. 5, the identification information acquisition portion 415 acquires from the person related to the newborn, second identification information for indicating the person related to the newborn (step S40).

The second newborn information acquisition portion 416 acquires second newborn living-body information from the newborn (step S41). The second newborn living-body information may be a fingerprint image. There may be acquired fingerprint images of the four fingers, that are the thumbs and forefingers of the baby's two hands.

The second determination portion 417 determines which one of a plurality of types of pattern is the one that the second newborn living-body information has (step S42). If the second newborn living-body information is the fingerprint image of the four fingers of the newborn, the second determination portion 417 may determine, for each of the four fingerprint images, which one of the plurality types of pattern (e.g., the P-arch, U-loop, R-loop, D-loop, P-whorl, unknown, T-arch, C-whorl, and A-whorl, as described above) is the one that the fingerprint image has. The second determination portion 417 may generate the sequence data of the pattern.

The first verification portion 4181 verifies the first identification information stored in the storage portion 221 with the second identification information (step S43).

The second verification portion 4182 verifies the first determination information associated with the first identification information having succeeded in the verification with the second identification information, with the second determination information indicating the determination result by the second determination portion 417 (step S44). The second verification portion 4182 may perform verification between the sequence data of the patterns.

[4-3: Technical Effectiveness of Information Processing Apparatus 4]

The information processing apparatus 4 according to the fourth example embodiment performs the verification for the person and the verification for the pattern. Therefore, even in a case of a newborn where it is difficult to collect data for high-accuracy verification, the information processing apparatus 4 is possible to perform high-accuracy verification. That is, the information processing apparatus 4 can guarantee a constant degree of verification accuracy, by carrying out the verification of the person related to the newborn, and then carrying out the verification of 1 to 1 (or, 1 to relatively small number) using the sequence data of the newborn related to the person.

Further, for example, considering a case that the first newborn living-body information is a fingerprint image, in a general fingerprint authentication the quality of data used for the authentication is critical. Therefore, the authentication with low-quality data is eliminated as FTA (Failure to Acquire). The body surface of a newborn is often covered with sebum, sheep water, etc. Thereby, in a general fingerprint authentication, it is highly likely that the authentication will be eliminated as FTA, and it is difficult to authenticate the newborn. On the other hand, the information processing apparatus 4 can realize high-accuracy verification, even in a case of a newborn where it is difficult to collect fingerprint images for high-accuracy verification, the information processing apparatus 4 is possible to perform high-accuracy verification. Because, the information processing apparatus 4 performs the verification for the person and the verification for the pattern that the fingerprint has.

5: Fifth Example Embodiment

A fifth example embodiment of an information processing apparatus, information processing method, and recording medium will be described. Hereinafter, there will be described the fifth example embodiment of the information processing apparatus, information processing method, and recording medium, using an information processing apparatus 5 to which the fifth example embodiment of the information processing apparatus, information processing method, and recording medium is applied.

[5-1: Configuration of Information Processing Apparatus 5]

Figure 6:
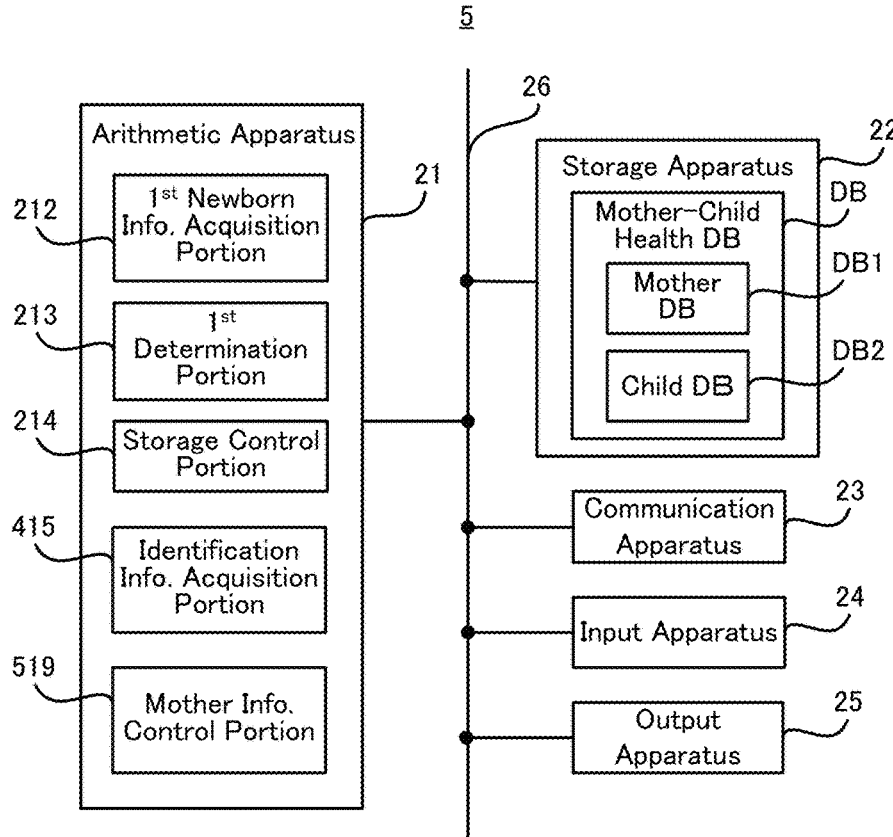
FIG. 6 is a block diagram illustrating a configuration of an information processing apparatus according to a fifth example embodiment.

Referring to FIG. 6, the configuration of the information processing apparatus 5 according to the fifth example embodiment will be described. FIG. 6 is a block diagram illustrating the configuration of the information processing apparatus 5 according to the fifth example embodiment.

As illustrated in FIG. 6, the information processing apparatus 5 according to the fifth example embodiment comprises the arithmetic apparatus 21 and the storage apparatus 22, similarly to at least one of the information processing apparatuses: from the information processing apparatus 2 according to the second example embodiment to the information processing apparatus 4 according to the fourth example embodiment. Furthermore, the information processing apparatus 5 may comprise the communication apparatus 23, the input apparatus 24, and the output apparatus 25, similarly to at least one of the information processing apparatuses: from the information processing apparatus 2 according to the second example embodiment to the information processing apparatus 4 according to the fourth example embodiment. However, the information processing apparatus 5 may not comprise at least one of the communication apparatus 23, the input apparatus 24, and the output apparatus 25. The information processing apparatus 5 according to the fifth example embodiment differs from at least one of the information processing apparatuses: from the information processing apparatus 2 according to the second example embodiment to the information processing apparatus 4 according to the fourth example embodiment, in that the arithmetic apparatus 21 further comprises a mother information control portion 519. The other features of the information processing apparatus 5 may be the same as those of at least one of the information processing apparatus from the information processing apparatus 2 according to the second example embodiment to the information processing apparatus 4 according to the fourth example embodiment. For this reason, different parts from the respective example embodiments already described, will be described in detail below, and with respect to other overlapping parts, the descriptions thereof will be omitted as appropriate.

[5-2: Information Processing Operation by Information Processing Apparatus 5]

In the fifth example embodiment, the person related to the newborn is the mother who delivered the newborn (hereafter, sometimes simply referred to as the "mother"). When the newborn is associated with a person related to the newborn, associating the newborn with the mother who delivered the newborn is most certain, and is helpful for identification of the newborn. For example, a mother may have one, two (twins) or three (triplets) newborns to be associated with herself. It is considered very few case that the pattern of the living-body information of each of the three newborns is the same as each other. Therefore, associating the newborn with the mother can be helpful for identification of the newborn. Also, in each scene where information of a newborn is operated, it is often appropriate to associate the newborn with the mother.

[5-2-1: Information Processing Operation When Pregnancy]

Figure 7:
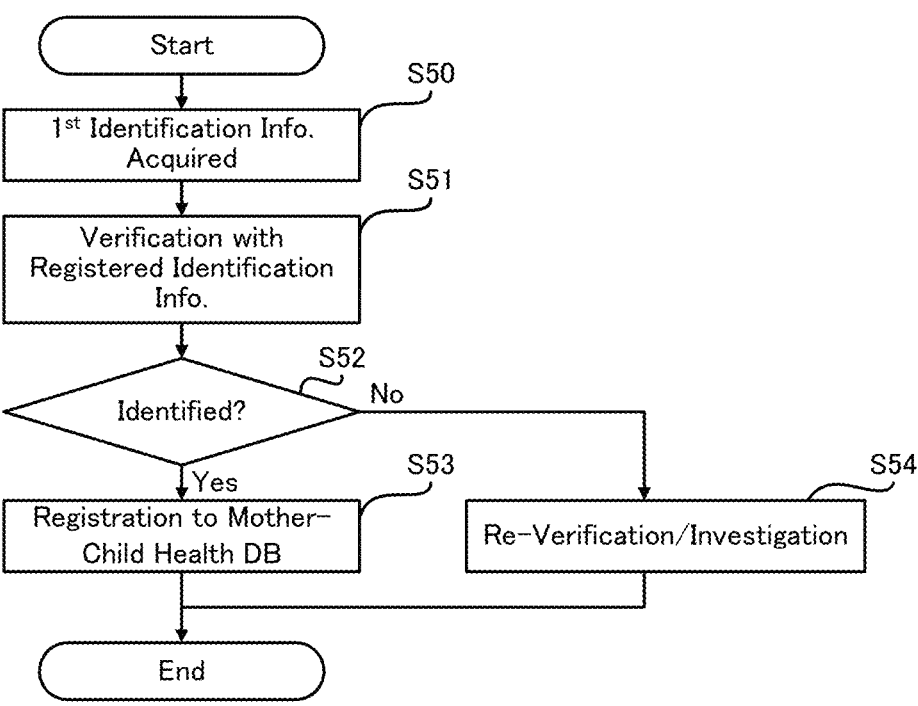
FIG. 7 is a flow chart illustrating a flow of an information processing operation performed by the information processing apparatus according to the fifth example embodiment at the moment when pregnant is determined.

FIG. 7 is a flow chart illustrating a flow of an information processing operation performed by the information processing apparatus 5 according to the fifth example embodiment when pregnancy has been determined.

As shown in FIG. 7, the identification information acquisition portion 415 acquires, from the mother, the first identification information for identifying the mother (step S50).

The mother information control portion 519 verifies registered identification information with the first identification information (step S51). The registered identification information may be, for example, information on all nationals, the information being for identifying each national and managed by the national government. The national may be a person who has the nationality of the country in which the information processing operation is being performed. The registered identification information may be registered in, for example, a national information DB in which the information on all nationals for identifying each national is registered, the information being managed by the national government.

The mother information control portion 519 determines whether or not the mother has been identified based on the verification result (step S52). If the mother has been identified (step S52: Yes), the mother information control portion 519 registers the first identification information in a mother-child health DB as the storage portion 221 (step S53). The mother-child health DB may include a mother DB1 and a child DB2. The mother information control portion 519 may register the first identification information in the mother DB1. When the registered identification information is information indicating the person having a nationality, the mother information control portion 519 may add information indicating that the nationality has been confirmed, in the identification information to be registered in the mother DB1.

If the mother has not been identified (step S52: No), the mother information control portion 519 performs a re-verification or investigation (step S54). For example, in a case of the verification by the identification information which is living-body information, the accuracy of the acquired living-body information may cause the verification to fail. Therefore, the re-verification may be performed. For example, if information of nationals having the nationality of the nation where the operation is implanted is registered as the registered identification information, the corresponding identification information may not exist. In this case, the nationality of the person may be investigated.

[5-2-2: Information Processing Before Delivery]

Figure 8:
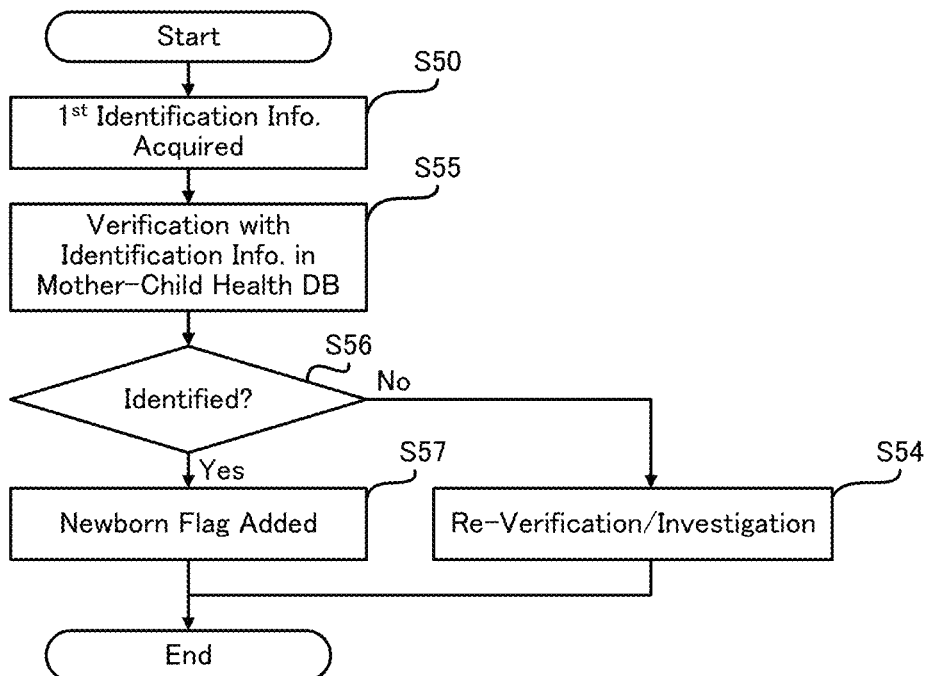
FIG. 8 is a flow chart illustrating a flow of an information processing operation performed by the information processing apparatus according to the fifth example embodiment before delivery.

FIG. 8 is a flow chart illustrating a flow of an information processing operation before delivery, the operation being performed by the information processing apparatus in the fifth example embodiment. The information processing operation before delivery may be performed later than the information processing operation when pregnancy is determined.

As shown in FIG. 8, the identification information acquisition portion 415 acquires, from the mother, the first identification information for identifying the mother (step S50).

The mother information control portion 519 verifies the identification information registered in the mother DB1 with the first identification information (step S55).

The mother information control portion 519 determines whether or not the mother has been identified based on the verification result (step S56). If the mother has been identified (step S56: Yes), the mother information control portion 519 adds a newborn flag in the identification information registered in the mother DB1 (step S57). The newborn flag may be a flag indicating that the newborn to which the nationality should be granted will be delivered.

If the mother has not been identified (step S56: No), the mother information control portion 519 performs a re-verification or investigation (step S54).

[5-2-3: Information Processing Operation After Delivery]

Figure 9:
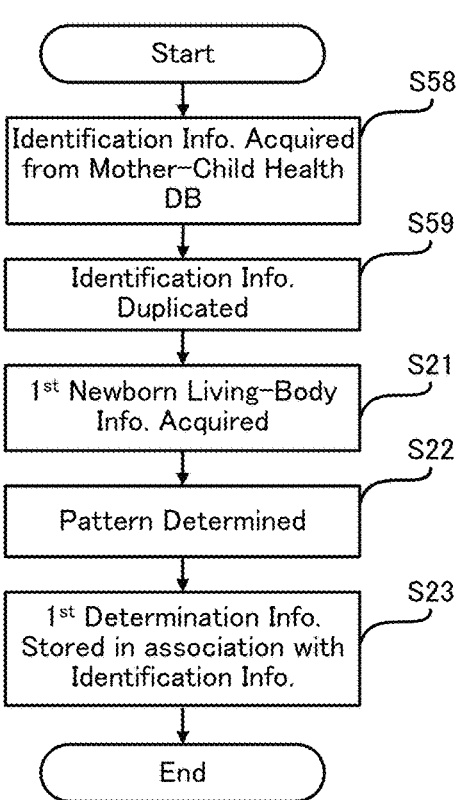
FIG. 9 is a flow chart illustrating a flow of an information processing operation performed by the information processing apparatus according to the fifth example embodiment after delivery.

FIG. 9 is a flow chart illustrating a flow of an information processing operation after delivery, the operation being performed by the information processing apparatus according to the fifth example embodiment. The information processing operation after delivery may be performed later than the information processing operation before delivery.

As shown in FIG. 9, the mother information control portion 519 acquires from the mother DB1, the identification information of the mother who has delivered the newborn (step S58). The mother information control portion 519 duplicates the identification information which was acquired on step S58 (step S59). The first newborn information acquisition portion 212 acquires the first newborn living-body information from the newborn (step S21). The first determination portion 213 determines which one of the plurality of types of pattern is the one that the first newborn living-body information has (step S22). By the storage control portion 214, the first determination information indicating the determination result by the first determination portion 213 is registered in the child DB2 in association with the identification information which was duplicated on step S59 (step S23).

The information of the newborn registered in the child DB2 may be, in the future, integrated into, for example, the national information DB in which the information on all nationals for identifying each national is registered, the information being managed by the national government. In the above-described example embodiment, although the case of registering the in formation of the mother in the mother DB1 and registering the information of the child in the child DB2 has been described, the management of the information of the mother by the mother DB1 may be terminated when the information of the child is registered in the child DB2.

In addition, although the mother DB1 and the child DB2 are provided separately in the description, the information of the mother and the information of the child may be registered in the same DB. In this case, the duplicating operation on step S59 may be omitted Further, in the present example embodiment, the person related to the newborn is described as the mother who has delivered the newborn. However, in a case that the person related to the newborn is a person other than the mother, the first identification information of the corresponding person who is other than the mother may be registered in the mother DB1. In this case, information indicating that the mother agrees that the information of the corresponding person who is other than the mother is registered in the mother DB1, may be added to the first identification information of the corresponding person, in the mother DB1. In addition, the information of the person other than the mother in the national information DB and the information of the person other than the mother in the mother DB1 may be correlated to each other. The person other than the mother may be, for example, the mother's husband, family, or the like.

[5-3: Technical Effectiveness of Information Processing Apparatus 5]

In the fifth example embodiment, since the person related to the newborn is the mother, the information processing apparatus 5 can identify the newborn more accurately.

6: Sixth Example Embodiment

A sixth example embodiment of an information processing apparatus, information processing method, and recording medium will be described. Hereinafter, there will be described the sixth example embodiment of the information processing apparatus, information processing method, and recording medium, using an information processing apparatus 6 to which the sixth example embodiment of the information processing apparatus, information processing method, and recording medium is applied.

The information processing apparatus 6 according to the sixth example embodiment differs from the information processing apparatuses: from the information processing apparatus 2 according to the second example embodiment to the information processing apparatus 5 according to the fifth example embodiment, in that the first identification information is living-body information of a person. The living-body information of the person may include, for example, information on a fingerprint of the person, information on a face of the person, information on an iris of the person, information on a voice of the person, and the like.

The other features of the information processing apparatus 6 may be the same as those of at least one of the information processing apparatuses: from the information processing apparatus 2 to the information processing apparatus 5. For this reason, different parts from the respective example embodiments already described, will be described in detail below, and with respect to other overlapping parts, the descriptions thereof will be omitted as appropriate.

In a case that one-to N verification (N may be relatively large) with a large scale N, is performed with using only the pattern data with respect to the pattern the newborn living-body information has, there is a problem with accuracy. Therefore, the accuracy of verification can be guaranteed by relating the pattern data with the living-body information of the person related to the newborn, especially of the mother. In other words, in a case that the living-body information is used, impersonation is difficult as compared with a case that the other identification information is used. Accordingly, the sixth example embodiment is advantageous in verification operation.

In particular, when a first living-body information as the first identification information stored in the mother DB1 is verified with a second living-body information as the second identification information acquired (the first verification), and then the first determination information relating to the first living-body information which has succeeded in the verification with the second living-body information acquired, is verified with the second determination information indicating the determination result by the second determination portion (the second verification), the verification with a high accuracy can be provided.

[Technical Effectiveness of Information Processing Apparatus 6]

Since the information processing apparatus 6 according to the sixth example embodiment uses the first identification information which the living-body information of a person, it is possible to further increase identification accuracy of the newborn.

7: Seventh Example Embodiment

A seventh example embodiment of an information processing apparatus, information processing method, and recording medium will be described. Hereinafter, there will be described the seventh example embodiment of the information processing apparatus, information processing method, and recording medium, using an information processing apparatus 7 to which the seventh example embodiment of the information processing apparatus, information processing method, and recording medium is applied.

[7-1: Configuration of Information Processing Apparatus 7]

Figure 10:
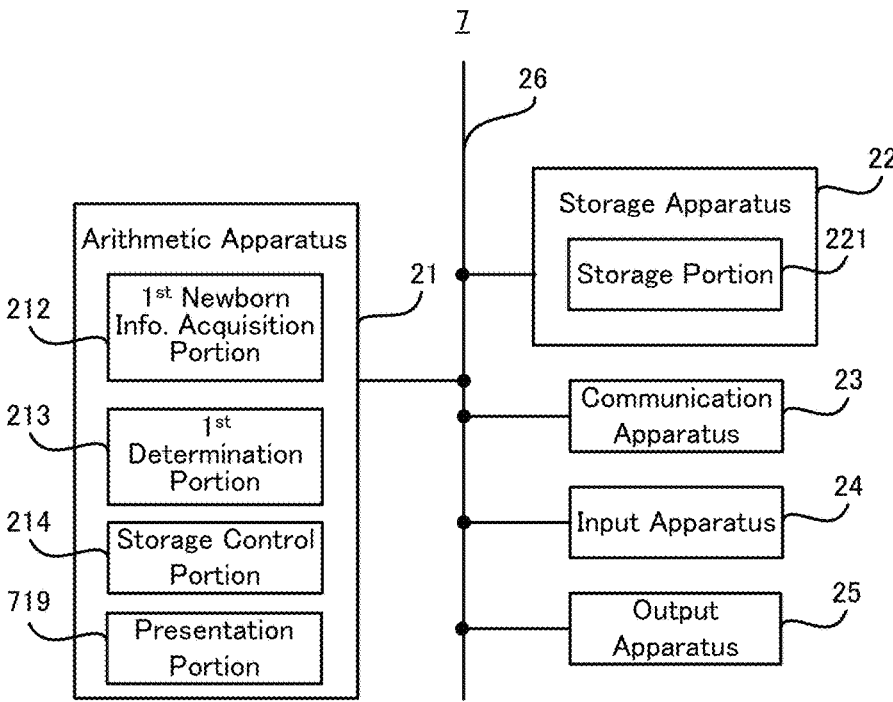
FIG. 10 is a block diagram illustrating a configuration of an information processing apparatus according to a seventh example embodiment.

Referring to FIG. 10, the configuration of the information processing apparatus 7 according to the seventh example embodiment will be described. FIG. 10 is a block diagram illustrating the configuration of the information processing apparatus 7 according to the seventh example embodiment.

As illustrated in FIG. 10, the information processing apparatus 7 according to the seventh example embodiment comprises the arithmetic apparatus 21 and the storage apparatus 22, similarly to at least one of the information processing apparatuses: from the information processing apparatus 2 according to the second example embodiment to the information processing apparatus 6 according to the sixth example embodiment. Furthermore, the information processing apparatus 7 may comprise the communication apparatus 23, the input apparatus 24, and the output apparatus 25, similarly to at least one of the information processing apparatuses: from the information processing apparatus 2 in the second example embodiment to the information processing apparatus 6 in the sixth example embodiment. However, the information processing apparatus 7 may not comprise at least one of the communication apparatus 23, the input apparatus 24, and the output apparatus 25. The information processing apparatus 7 according to the seventh example embodiment differs from at least one of the information processing apparatuses: from the information processing apparatus 2 in the second example embodiment to the information processing apparatus 6 in the sixth example embodiment, in that arithmetic apparatus 21 further comprises a presentation portion 719, and a storage control operation performed by the storage control portion 214. The other features of the information processing apparatus 7 may be the same as those of at least one of the information processing apparatuses: from the information processing apparatus 2 in the second example embodiment to the information processing apparatus 6 in the sixth example embodiment. For this reason, different parts from the respective example embodiments already described, will be described in detail below, and with respect to other overlapping parts, the descriptions thereof will be omitted as appropriate.

[7-2: Storage Control Operation by Information Processing Apparatus 7]

Figure 11:
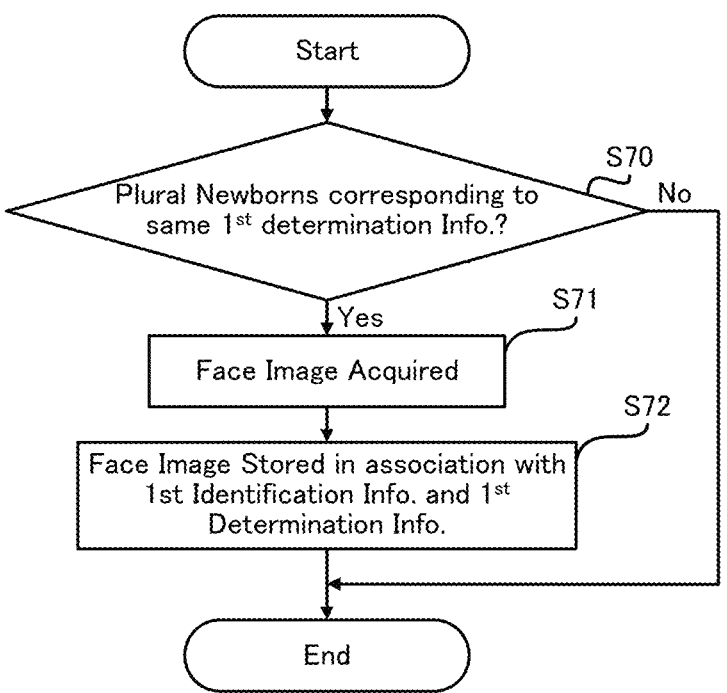
FIG. 11 is a flow chart illustrating a flow of an information processing operation performed by the information processing apparatus according to the seventh example embodiment.

Referring to FIG. 11, a flow of the information processing operation performed by the information processing apparatus 7 according to the seventh example embodiment will be described. FIG. 11 is a flow chart illustrating the flow of the storage control operation that is performed by the information processing apparatus 7 according to the seventh example embodiment. The storage control operation may be an operation corresponding to a modification of the storage control operation in the second example embodiment described above (i.e., the operation on step S23 in FIG. 3).

As shown in FIG. 11, the storage control portion 214 determines whether or not there are a plurality of newborns corresponding to the same first determination information within a predetermined range of time-space (step S70). The predetermined range of time-space may include the same arrangement in a hospital.

When there are the plurality of newborns corresponding to the same first determination data within the predetermined range of time-space (step S70: Yes), the storage control portion 214 acquires a face image of the corresponding newborn (step S71). The storage control portion 214 causes the storage portion 221 to store the first identification information and first determination information with respect to the corresponding newborn in association with the face image of the corresponding newborn.

[7-3: Operation at Verification by Information Processing Apparatus 7]

In a case the verification of the corresponding newborn by the verification portion 418 is performed, the presentation portion 719 presents the operator with the face image of the corresponding newborn stored in the storage portion 221, to prompt the operator to do a confirmation operation with respect to the face of the corresponding newborn. The time when the verification of the corresponding newborn is performed by the verification portion 418, may be the time when the newborn leaves from hospital. By the operation for confirming the newborn's face visually by the operator, the occurrence of newborn mix-ups can be prevented.

The information processing apparatus 7 may further perform authentication using a face image. The authentication using a face image may be the facial authentication using living-body information extracted from a collected face image, or the iris authentication. In addition, the information processing apparatus 7 may perform authentication by fingerprint authentication and the like, the finger print authentication using fingerprint information collected for pattern authentication. The information processing apparatus 7 may perform the verification of the face image stored in the storage portion 221 with the face image of the newborn acquired at the timing when the verification is performed by the verification portion 418, for example. That is, the information processing apparatus 7 may perform the multimodal authentication.

[7-4: Technical Effectiveness of Information Processing Apparatus 7]

The information processing apparatus 7 according to the seventh example embodiment can identify the newborn more reliably and, thereby, can prevent the occurrence of newborn mix-ups.

8: Eighth Example Embodiment

An eighth example embodiment of an information processing apparatus, information processing method, and recording medium will be described. Hereinafter, there will be described the eighth example embodiment of the information processing apparatus, information processing method, and recording medium, using an information processing apparatus 8 to which the eighth example embodiment of the information processing apparatus, information processing method, and recording medium is applied.

The information processing apparatus 8 according to the eighth example embodiment differs from the information processing apparatus 4 according to the fourth example embodiment, in the determination operation performed by the first determination portion 213, the storage control operation performed by the storage control portion 214, the determination operation performed by the second determination portion 417, and the verification operation performed by the second verification portion 4182. The other features of the information processing apparatus 8 may be the same as those of the information processing apparatus 4. For this reason, different parts from the respective example embodiments already described, will be described in detail below, and with respect to other overlapping parts, the descriptions thereof will be omitted as appropriate.

FIGS. 12A and 12B shows flow charts, each illustrating a flow of the information processing operation performed by the information processing apparatus according to the eighth example embodiment.

[8-1: Information Processing Operation at Storing by Information Processing Apparatus 8]

As shown in FIG. 12A, the storage portion 221 stores the first identification information for indicating the person related to the newborn (step S20). The first newborn information acquisition portion 212 acquires the first newborn living-body information from the newborn (step S21). The first determination portion 213 determines which one of the predetermined plurality of types of pattern is the one that the first newborn living-body information has (step S22).

Figure 13:
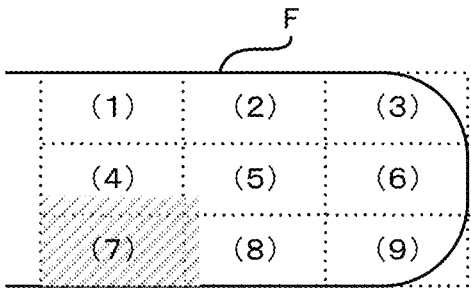
FIG. 13 is a conceptual diagram illustrating an information processing operation performed by the information processing apparatus according to the eighth example embodiment.

The first determination portion 213 divides the first newborn living-body information into a plurality of portions, and determines from which part the pattern of the first newborn living-body information has been detected (step S80). The first newborn living-body information may be a fingerprint image. In this case, as exemplified in FIG. 13, the first determination portion 213 may divide the fingerprint image F into 3×3, that is, 9 areas, for example. the first determination portion 213 may specify which area of the fingerprint F the pattern (also referred to as a "printed pattern") in the fingerprint image, has been determined mainly from. The printed pattern may be the same as or different from the fingerprint pattern described above. The printed pattern may be the most clearly discriminable pattern in a certain finger. In the example shown in FIG. 13, the pattern in the area (7) is most clearly discriminable. In this case, the first determination portion 213 may specify that the printed pattern has been determined mainly from the fingerprint image corresponding to the area (7).

The storage control portion 214 adds part information related to the part determined by the first determination portion 213 in the first determination information and causes the storage portion 221 to store the first determination information in association with the first identification information (step S81). In the example shown in FIG. 13, the pattern in the area (7) is the most clearly discriminable. In this case, the storage control portion 214 may add information indicating that the pattern has been determined from the fingerprint image corresponding to the area (7) to the information indicating the printed pattern that is allowed to be determined from the fingerprint image corresponding to the area (7), and cause the storage portion 221 to store the added information. For example, as shown in Table #1 below, the storage control portion 214 may causes the storage portion 221 to store: information indicating ID of the newborn; the printed pattern of the fingerprint image: and information indicating the area as the part information.

TABLE #1

| ID | AREA | DESIGN PATTERN |
|---|---|---|
| 000001 | (7) | A |
| 000002 | (5) | B |
| 000003 | NUL | NUL |
| 000004 | (5) | C |

The above Table #1 may show that: with respect to the newborn of ID"000001", the printed pattern was determined from the fingerprint image corresponding to the area (7) and the printed pattern is "A"; with respect to the newborn of ID"000002", the printed pattern was determined from the fingerprint image corresponding to the area (5) and the printed pattern is "B"; with respect to the newborn of ID"000003", the printed pattern was not determined; and with respect to the newborn of ID"000004", the printed pattern was determined from the fingerprint image corresponding to the area (5) and the printed pattern is "C".

[8-2: Information Processing Operation at Verification by Information Processing Apparatus 8]

As illustrated in FIG. 12B, the identification information acquisition portion 415 acquires the second identification information for indicating the person related to the newborn (step S40). The second newborn information acquisition portion 416 acquires the second newborn living-body information from the newborn (step S41). The second determination portion 417 determines which one of the plurality of types of pattern is the one that the second newborn living-body information has (step S42).

The second determination portion 417 divides the second newborn living-body information into a plurality of parts, and determines from which part the pattern of the second newborn living-body information is detected (step S82). The second newborn living-body information may be a fingerprint image. In this case, similarly to the operation of the first determination portion 213, the second determination portion 417 may divide the fingerprint image F into the 9 areas of 3×3, for example. The second determination portion 417 may specify which area of the fingerprint image the printed pattern has been determined mainly from.

The first verification portion 4181 verifies the first identification information stored in the storage portion 221 with the second identification information (step S43).

The second verification portion 4182 verifies the first determination information associated with the first identification information having succeeded in the verification with the second identification information, with the second determination information where the part information related to the part determined by the second determination portion 417 is added (step S83). In the first determination information, the part information related to the part determined by the first determination portion 213 may be added. The above Table #1 may show the first determination information associated with the first identification information that succeeded in the verification with the second identification information. In this case, newborns related to the person corresponding to the identification information may be four to whom "ID"000001", "ID"000002", "ID"000003", and "ID"000004" are given respectively. For example, when the area determined by the second determination portion 417 is "(7)," the second verification portion 4182 may verify the printed pattern of ID"000001" with the printed pattern determined by the second determination portion 417. For example, when the area determined by the second determination portion 417 is "(5)", the second verification portion 4182 may verify the printed pattern of ID"000002" and the printed pattern of ID"000004" with the printed pattern determined by the second determination portion 417.

[8-3: Technical Effectiveness of Information Processing Apparatus 8]

Since the information processing apparatus 8 according to the eighth example embodiment adds the part information related to the part, the information processing apparatus 8 can provide the verification with higher accuracy even when the number of newborns is relatively large.

9: Ninth Example Embodiment

A ninth example embodiment of an information processing apparatus, information processing method, and recording medium will be described. Hereinafter, there will be described the ninth example embodiment of the information processing apparatus, information processing method, and recording medium, using an information processing apparatus 9 to which the ninth example embodiment of the information processing apparatus, information processing method, and recording medium is applied.

[9-1: Configuration of Information Processing Apparatus 9]

Figure 14:
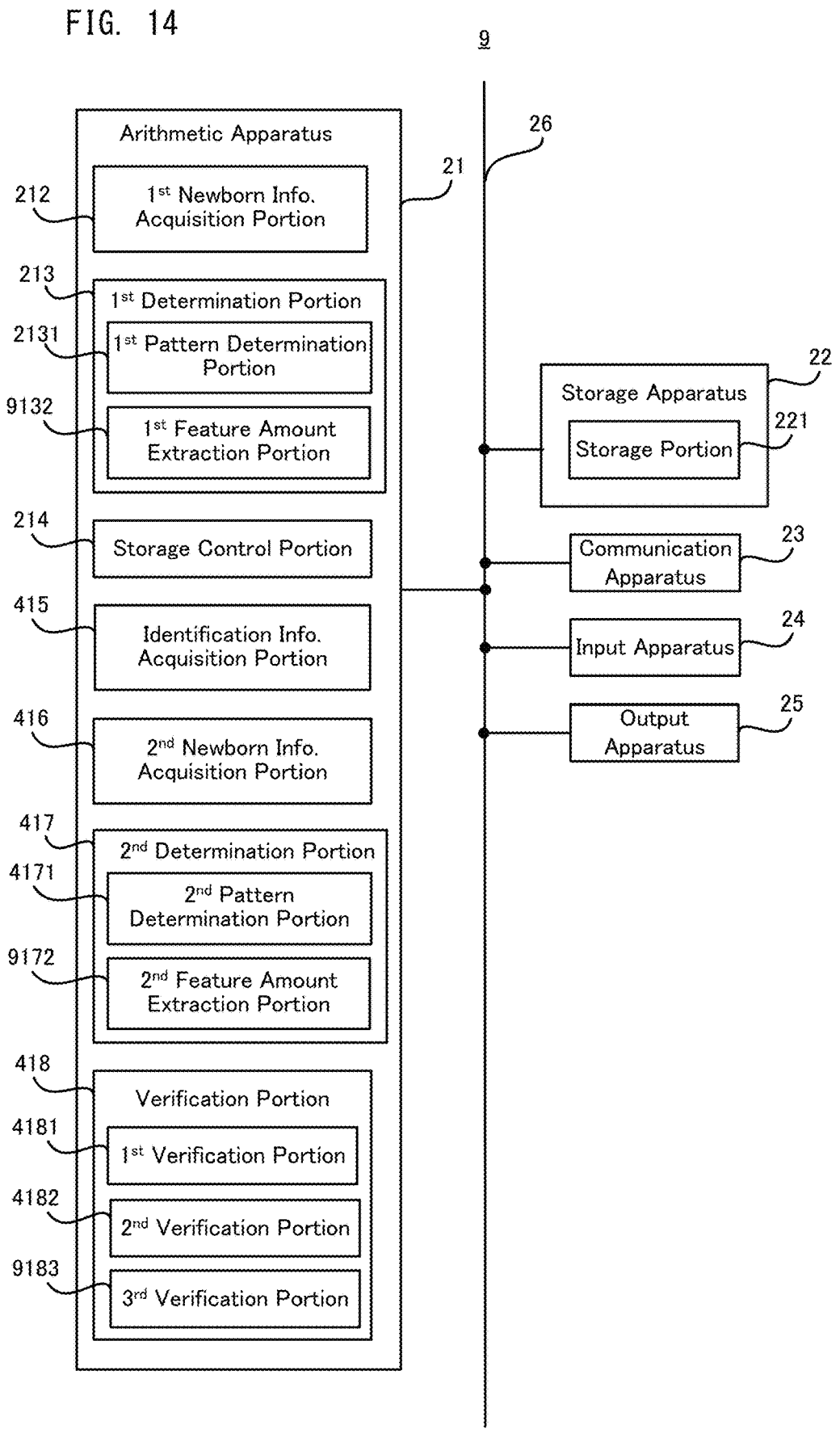
FIG. 14 is a block diagram illustrating a configuration of an information processing apparatus according to the ninth example embodiment.

Referring to FIG. 14, the configuration of the information processing apparatus 9 according to the ninth example embodiment will be described. FIG. 14 is a block diagram illustrating the configuration of the information processing apparatus 9 according to the ninth example embodiment.

As shown in FIG. 14, the information processing apparatus 9 according to the ninth example embodiment comprises the arithmetic apparatus 21 and the storage apparatus 22, similarly to the information processing apparatus 4 according to the fourth example embodiment and the information processing apparatus 8 according to the eighth example embodiment. Furthermore, the information processing apparatus 9 may comprise the communication apparatus 23, the input apparatus 24, and the output apparatus 25, similarly to the information processing apparatus 4 in the fourth example embodiment and the information processing apparatus 8 in the eighth example embodiment. However, the information processing apparatus 9 may not comprise at least one of the communication apparatus 23, the input apparatus 24, and the output apparatus 25. The information processing apparatus 9 according to the ninth example embodiment differs from the information processing apparatus 4 according to the fourth example embodiment and the information processing apparatus 8 according to the eighth example embodiment, in that the first determination portion 213 comprises a first feature-amount extraction portion 9132 as well as the first pattern determination portion 2131, the second determination portion 417 comprises the second feature-amount extraction portion 9172 as well as the second pattern determination portion 4171, and the verification portion 418 comprise the third verification portion 9183. The other features of the information processing apparatus 9 may be the same as those of the information processing apparatus 4 according to the fourth example embodiment and the information processing apparatus 8 according to the eighth example embodiment. For this reason, different parts from the respective example embodiments already described, will be described in detail below, and with respect to other overlapping parts, the descriptions thereof will be omitted as appropriate.

[9-2: Information Processing Operation at Storing by Information Processing Apparatus 9]

Figures 15, 16:
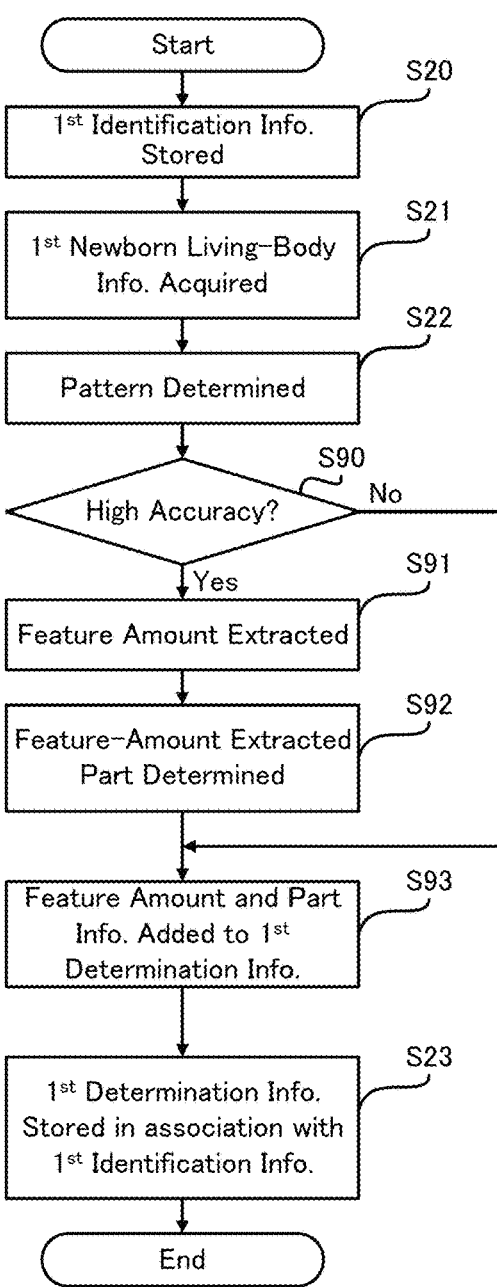
FIG. 15 is a flow chart illustrating a flow of an information processing operation performed by the information processing apparatus according to the ninth example embodiment at the moment of recoding.
FIG. 16 is a conceptual diagram illustrating an information processing operation performed by the information processing apparatus according to the ninth example embodiment.

Referring to FIG. 15, a flow of the information processing operation at storing performed by the information processing apparatus 9 in the ninth example embodiment will be described. FIG. 15 is a flow chart illustrating the flow of the information processing operation at storing performed by the information processing apparatus 9 according to the ninth example embodiment.

As shown in FIG. 15, the storage portion 221 stores the first identification information for identifying the person related to the newborn (step S20). The first newborn information acquisition portion 212 acquires the first newborn living-body information from the newborn (step S21). The first determination portion 213 determines which one of the predetermined plurality of types of pattern is the one that the first newborn living-body information has (step S22).

The first determination portion 213 determines whether or not the first newborn living-body information has accuracy higher than a predetermined accuracy (step S90). When the first newborn living-body information has higher accuracy than the predetermined accuracy (step S90: Yes), the first feature-amount extraction portion 9132 extracts the feature amount from the first newborn living-body information, in addition to the determination of the pattern of the first newborn living-body information by the first pattern determination portion 2131 (step S91).

The first feature-amount extraction portion 9132 divides the first newborn living-body information into a plurality of parts, and determines from which part the first newborn living-body information having accuracy higher than the predetermined accuracy has been detected (step S92). The first newborn living-body information may be a fingerprint image. In this case, as exemplified in FIG. 16, the first feature-amount extraction portion 9132 may divide the fingerprint image F into 3×3, that is, 9 areas, for example. The first feature-amount extraction portion 9132 may specify from which area of the fingerprint image F the feature amount has been extracted. In the example shown in FIG. 16, the feature amount can be extracted in the area (7). In this case, the first feature-amount extraction portion 9132 may specify that the feature amount was extracted from the area (7).

When the first feature-amount extraction portion 9132 extracts the feature amount from the first newborn living-body information, the storage control portion 214 includes the feature amount and part information indicating a part where the feature amount was extracted in the first determination information (step S93). The storage control portion 214 causes the storage portion 221 to store the first determination information in association with the first identification information (step S23). In the example shown in FIG. 16, the feature amount can be extracted in the area (7). In this case, the storage control portion 214 may include information indicating the feature amount and the area (7) where the feature amount was extracted in the first determination information, and cause the storage portion 221 to store the first determination information. For example, as shown in Table 2 below, the storage control portion 214 may causes the storage portion 221 to store: information indicating the ID of the newborn; the pattern the fingerprint image has; the feature amount; and the area where the feature amount was extracted.

TABLE #2

| ID | PATTERN | FEATURE AMOUNT | FEATURE AMOUNT AREA |
|--------|---------|---------------|---------------------|
| 000001 | A | X | (7) |
| 000002 | B | NUL | NUL |
| 000003 | NUL | NUL | NUL |
| 000004 | C | Y | (5) |

The above Table #2 may indicate that with respect to the newborn of ID"000001, the pattern is "A", the feature amount is "X", and the feature amount was extracted in the area "(7)". Also, the above Table #2 may indicate that with respect to the newborn of ID"000002, the pattern is "B", and the feature amount was not extracted. Also, the above Table #2 may indicate that with respect to the newborn of ID"000003, the pattern was not determined, and the feature amount was not extracted. Also, the above Table #2 may indicate that with respect to the newborn of ID"000004, the pattern is "C", the feature amount is "Y", and the feature amount was extracted in the area "(5)".

[9-3: Information Processing Operation at Verification by Information Processing Apparatus 9]

Figure 17A:
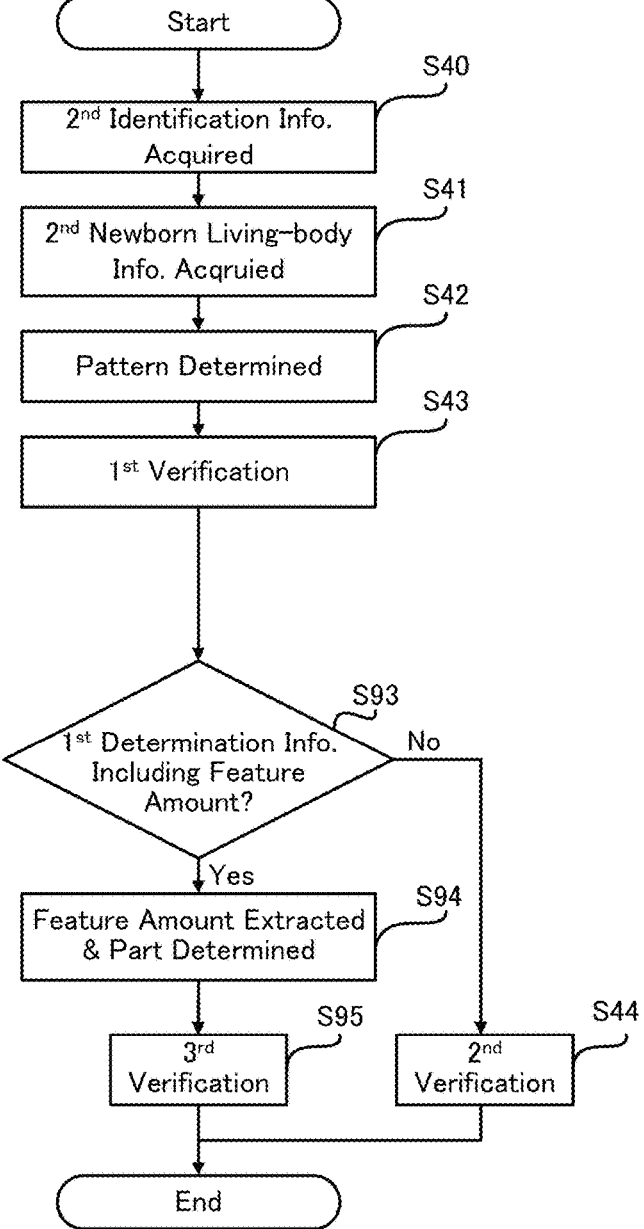
FIG. 17A includes flow charts, each illustrating a flow of an information processing operation performed by the information processing apparatus according to the ninth example embodiment at the moment of verification.
Figure 17B:
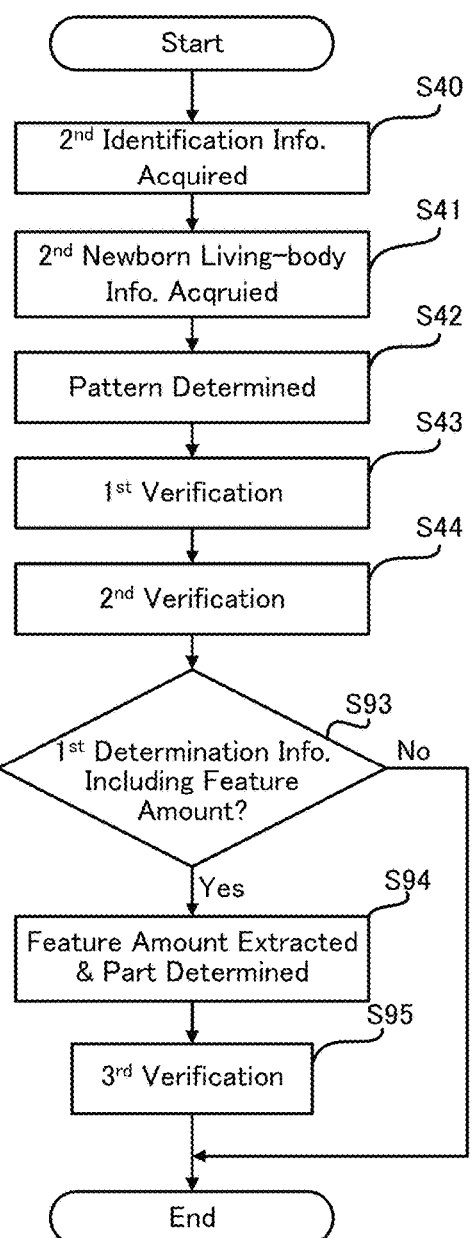
FIG. 17B includes flow charts, each illustrating a flow of an information processing operation performed by the information processing apparatus according to the ninth example embodiment at the moment of verification.

Referring to FIGS. 17A and 17B, a flow of the information processing operation at verification performed by the information processing apparatus 9 according to the ninth example embodiment, will be described. FIGS. 17A and 17B includes flow charts, each illustrating the flow of the information processing operation at verification performed by the information processing apparatus 9 in the ninth example embodiment.

As illustrated in FIG. 17A, the identification information acquisition portion 415 acquires from the person related to the newborn, the second identification information for indicating the person related to the newborn (step S40). The second newborn information acquisition portion 416 acquires the second newborn living-body information from the newborn (step S41). The second pattern determination portion 4171 determines which one of the plurality of types of pattern is the one that the second newborn living-body information has (step S42). The first verification portion 4181 verifies the first identification information stored in the storage portion 221 with the second identification information (step S43).

The verification portion 418 determines whether or not the first determination information includes the feature amount (step S93). When the first determination information includes the feature amount (step S93: Yes), the second feature amount extraction portion 9172 divides the second newborn living-body information into a plurality of portions, extracts the feature amount, and determines from which part the feature amount has been detected (step S94). The second newborn living-body information may be a fingerprint image. In this case, similarly to the operation by the first feature-amount extraction portion 9132, the second feature-amount extraction portion 9172 may divide the fingerprint image F into 3×3, that is, 9 areas, for example. The second feature-amount extraction portion 9172 may specify from which area of the fingerprint image the feature amount has been extracted.

The third verification portion 9183 performs the verification of the feature amount (step S94). The third verification portion 9183 may verify with the second determination information, the first determination information associated with the first identification information that has succeeded in the verification with the second identification information. In the first determination information, the feature amount extracted by the first feature-amount extraction portion 9132 and the part information on the part determined by the first feature-amount extraction portion 9132, may be added. The second determination information may be information where the feature amount extracted by the second feature-amount extraction portion 9172 and the part information on the part determined by the second feature-amount extraction portion 9172 are added. The above Table #2 may show the first determination information associated with the first identification information that succeeded in the verification with the second identification information. In this case, the newborns relating to the person corresponding to the identification information may be four: "ID"000001"; "ID"000002"; "ID"000003"; and "ID"000004". For example, when the area determined by the second feature-amount extraction portion 9172 is "(7)," the third verification portion 9183 may verify the feature amount of ID"000001" with the feature amount extracted by the second feature-amount extraction portion 9172. For example, when the area determined by the second feature-amount extraction portion 9172 is "(5)," the third verification portion 9183 may verify the feature amount of ID"000004" with the feature amount extracted by the second feature-amount extraction portion 9172.

When the first determination information does not include the feature amount (step S93: No), the second verification portion 4182 verifies the first determination information associated with the first identification information that has succeeded in the verification with the second identification information, with the second determination information indicating the determination result by the second pattern determination portion 4171 (step S44).

Further, instead of the flow of the information processing operation shown in FIG. 17A, the flow of the information processing operation shown in FIG. 17B may be performed. That is, regardless of the determination result on step S93, the operation on step S44 may be performed. That is, the information processing apparatus 9 may perform the fusion verification.

Similarly to the eighth example embodiment, also in the ninth example embodiment, the first pattern determination portion 2131 divides the first newborn living-body information into a plurality of parts, and determines from which part the pattern that the first newborn living-body information has was detected. In this case, the second pattern determination portion 4171 divides the second newborn living-body information into a plurality of parts, and determines from which part the pattern that the second newborn living-body information has was detected. The second verification portion 4182 may verify the first determination information where the part information on the part determined by the first pattern determination portion 2131 was added, with the second determination information where the part information on the part determined by the second pattern determination portion 4171 was added.

[9-4: Technical Effectiveness of Information Processing Apparatus 9]

The information processing apparatus 9 according to the ninth example embodiment can perform at least one of the verification of the pattern and the verification of the feature amount when the first determination information includes the feature amount, and thereby, can verify the newborn more accurately.

In the above-described example embodiments, a fingerprint image is exemplified as the newborn living-body information. However, the newborn living-body information may be living-body information other than the fingerprint image. As the newborn living-body information, for example, a pattern image of the bottom of newborn's foot may be applied.

In the above-described example embodiments, for example, at an opportunity such as vaccination, the fingerprint image of a target person may be acquired and the acquired fingerprint image may be additionally registered in the mother DB1. When the acquired fingerprint image is subject to a quality check, and has a quality that could be used for general fingerprint authentication for adults, the authentication of the target person may be updated to more accurate authentication. The quality check of the fingerprint image may be, by extracting the feature information from the fingerprint image, executed based on the feature information extracted. Accompanying this, the verification using the identification information of the mother is unnecessary at the moment of the verification of the target person, and thereby, it is possible to reduce the mother's burden. Furthermore, the first determination information of the newborn as the target person may be integrated into, for example, the national information DB in which the information on all nationals for identifying each national is registered, the information being managed by the national government.

10: Supplementary Note

With respect to the example embodiments described above, the following supplementary notes are further disclosed.

[Supplementary Note 1]

An information processing apparatus comprising: a storage unit that is configured to store first identification information for indicating a person related to a newborn; a first newborn information acquisition unit that is configured to acquire first newborn living-body information from the newborn; a first determination unit that is configured to determine which one of predetermined plurality types of pattern is a type of pattern that the first newborn living-body information has; and a storage control unit that is configured to cause the storage unit to store first determination information indicating a determination result by the first determination unit in association with the first identification information.

[Supplementary Note 2]

The information processing apparatus according to the supplementary note 1, wherein the first newborn information acquisition unit is configured to acquire at least two pieces of the first newborn living-body information from the newborn, the first determination unit is configured to, for each of the at least two pieces of the first newborn living-body information, determine which one of the plurality types of pattern is the type of pattern that the first newborn living-body information has, and the storage control unit is configured to cause the storage unit to store in association with the first identification information, the first determination information in which the determination result by the first determination unit corresponding to each of the at least two pieces of the first newborn living-body information is combined with each other.

[Supplementary Note 3]

The information processing apparatus according to the supplementary note 1 or 2, wherein the first newborn living-body information is a fingerprint image.

[Supplementary Note 4]

The information processing apparatus according to the supplementary note 1 or 2, further comprising: an identification information acquisition unit that is configured to acquire from the person related to the newborn, second identification information for indicating the person related to the newborn; a second newborn information acquisition unit that is configured to acquire second newborn living-body information from the newborn; a second determination unit that is configured to determine which one of the plurality of types of pattern is a type of pattern that the second newborn living-body information has; and a verification unit including a first verification unit and a second verification unit: the first verification unit being configured to verify the first identification information stored in the storage unit with the second identification information; and the second verification unit being configured to verify the first determination information associated with the first identification information that has succeeded in verification with the second identification information with the second determination information indicating a determination result by the second determination unit.

[Supplementary Note 5]

The information processing apparatus according to the supplementary note 1 or 2, wherein the person related to the newborn is a mother who gives birth to the newborn.

[Supplementary Note 6]

The information processing apparatus according to the supplementary note 1 or 2, wherein the first identification information is living-body information of the person.

[Supplementary Note 7]

The information processing apparatus according to the supplementary note 4, wherein the storage control unit is configured to, when a plurality of newborns are corresponding to the same first determination information within a predetermined range of time-space, cause the storage unit to store the first identification information and first determination information with respect to each of the plurality of newborns in association with a face image of the corresponding newborn, and the information processing apparatus further comprises a presentation unit that is configured to present to an operator, the face image of the corresponding newborn stored in the storage unit, at time of verification for the corresponding newborn by the verification unit, and to prompt the operator to do a confirmation operation with respect to a face of the corresponding newborn.

[Supplementary Note 8]

The information processing apparatus according to the supplementary note 4, wherein the first determination unit is configured to divide the first newborn living-body information into a plurality of parts, and determine which part the pattern of the first newborn living-body information has been detected from, the storage control unit is configured to add in the first determination information, part information on the part determined by the first determination unit, and to cause the storage unit to store the first determination information in association with the first identification information, the second determination unit is configured to divide the second newborn living-body information into a plurality of parts, and determine which part the pattern of the second newborn living-body information has been detected from, and the second verification unit is configured to verify the first determination information associated with the first identification information that has succeeded in the verification with the second identification information, with the second determination information where part information of the part determined by the second determination unit has been added.

[Supplementary Note 9]

The information processing apparatus according to the supplementary note 4, wherein the first determination unit is configured to extract, when the first newborn living-body information has higher accuracy than a predetermined accuracy, a feature amount from the first newborn living-body information as well as a determination of the pattern the first newborn living-body information has, the storage control unit is configured to, when the first determination unit has extracted the feature amount from the first newborn living-body information, cause the storage unit to store the first determination information including the feature amount in association with the first identification information, and the verification unit is configured to, when the first determination information includes the feature amount, execute at least one of verification of the pattern and verification of the feature amount.

[Supplementary Note 10]

An information processing method comprising: storing first identification information for indicating a person related to a newborn in a storage unit; acquiring first newborn living-body information from the newborn; determining which one of predetermined plurality types of pattern is a type of pattern that the first newborn living-body information has; and causing the storage unit to store first determination information indicating a determination result in association with the first identification information.

[Supplementary Note 11]

A recording medium on which a computer program that allows a computer to execute an information processing method is recorded, the information processing method comprising: storing first identification information for indicating a person related to a newborn in a storage unit; acquiring first newborn living-body information from the newborn; determining which one of predetermined plurality types of pattern is a type of pattern that the first newborn living-body information has; and causing the storage unit to store first determination information indicating a determination result in association with the first identification information.

At least a part of the constituent components of the above-described example embodiments can be appropriately combined with at least the other part of the constituent components of the above-described example embodiments. A part among the constituent components of the above-described example embodiments may not be used.

This disclosure is not limited to the above example embodiments. This disclosure may be modified as appropriate in range of a range which is not contrary to the technical idea which can be read from the whole of the description and the claims. The information processing apparatus, information processing method, and recording medium with such modifications are also included in the technical idea of this disclosure. Also, to the extent permitted by law, all publications and theses described in the present description are incorporated herein.

To the extent permitted by law, this application claims priority based on Japanese application No. 2022-085036, filed May 25, 2022, the entire disclosure of which is incorporated herein.

DESCRIPTION OF REFERENCE SIGNS

1,2,3,4,5,6,7,8,9 Information processing apparatus
11,221 Storage Apparatus
12,212 First newborn information acquisition portion
13,213 First determination portion
14,214 Storage control portion
415 Identification information acquisition portion
416 Second newborn information acquisition portion
417 Second determination portion
418 Verification portion
4181 First verification portion
4182 Second verification portion
519 Mother information control portion
719 Presentation portion
9183 Third verification portion
2131 First pattern determination portion
9132 First feature amount extraction portion
4171 Second pattern determination portion
9172 Second feature amount extraction portion

What is claimed is:

1. An information processing apparatus comprising:
at least one memory configured to store instructions; and
at least one processor configured to execute the instructions to:
store first identification information for indicating a person related to a newborn in a storage unit;
acquire first newborn living-body information from the newborn;
determine which one of predetermined plurality types of pattern is a type of pattern that the first newborn living-body information has; and
cause the storage unit to store first determination information indicating a determination result with respect to the first newborn living-body information in association with the first identification information,
wherein the at least one processor is further configured to execute the instructions to:
acquire at least two pieces of the first newborn living-body information from the newborn;
for each of the at least two pieces of the first newborn living-body information, determine which one of the plurality types of pattern is the type of pattern that the first newborn living-body information has; and
cause the storage unit to store in association with the first identification information, the first determination information in which the determination result corresponding to each of the at least two pieces of the first newborn living-body information is combined with each other.

2. The information processing apparatus according to claim 1, wherein
the first newborn living-body information is a fingerprint image.

3. The information processing apparatus according to claim 1, wherein the at least one processor is further configured to execute the instructions to:

acquire from the person related to the newborn, second identification information for indicating the person related to the newborn;

acquire second newborn living-body information from the newborn;

determine which one of the plurality of types of pattern is a type of pattern that the second newborn living-body information has;

verify the first identification information stored in the storage unit with the second identification information; and verify the first determination information associated with the first identification information that has succeeded in verification with the second identification information with the second determination information indicating a determination result with respect to the second newborn living-body information.

4. The information processing apparatus according to claim 3, wherein the at least one processor is further configured to execute the instructions to:

when a plurality of newborns are corresponding to the same first determination information within a predetermined range of time-space, cause the storage unit to store the first identification information and first determination information with respect to each of the plurality of newborns in association with a face image of the corresponding newborn; and present to an operator, the face image of the corresponding newborn stored in the storage unit, at time of verification for the corresponding newborn to prompt the operator to do a confirmation operation with respect to a face of the corresponding newborn.

5. The information processing apparatus according to claim 3, wherein the at least one processor is further configured to execute the instructions to:

divide the first newborn living-body information into a plurality of parts; determine which part the pattern of the first newborn living-body information has been detected from;

add in the first determination information, part information on the part determined with respect to the first newborn living-body information; cause the storage unit to store the first determination information in association with the first identification information;

divide the second newborn living-body information into a plurality of parts; determine which part the pattern of the second newborn living-body information has been detected from; and verify the first determination information associated with the first identification information that has succeeded in the verification with the second identification information, with the second determination information where part information of the part determined with respect to the second newborn living-body information has been added.

6. The information processing apparatus according to claim 3, wherein the at least one processor is further configured to execute the instructions to:

extract, when the first newborn living-body information has higher accuracy than a predetermined accuracy, a feature amount from the first newborn living-body information as well as a determination of the pattern the first newborn living-body information has;

when the feature amount has been extracted from the first newborn living-body information, cause the storage unit to store the first determination information including the feature amount in association with the first identification information; and when the first determination information includes the feature amount, execute at least one of verification of the pattern and verification of the feature amount.

7. The information processing apparatus according to claim 1, wherein the person related to the newborn is a mother who gives birth to the newborn.

8. The information processing apparatus according to claim 1, wherein the first identification information is living-body information of the person.

9. An information processing method comprising:

storing first identification information for indicating a person related to a newborn in a storage unit;

acquiring first newborn living-body information from the newborn;

determining which one of predetermined plurality types of pattern is a type of pattern that the first newborn living-body information has; and causing the storage unit to store first determination information indicating a determination result in association with the first identification information, wherein the information processing method further comprises:

acquiring at least two pieces of the first newborn living-body information from the newborn;

for each of the at least two pieces of the first newborn living-body information, determining which one of the plurality types of pattern is the type of pattern that the first newborn living-body information has; and causing the storage unit to store in association with the first identification information, the first determination information in which the determination result corresponding to each of the at least two pieces of the first newborn living-body information is combined with each other.

10. A non-transitory recording medium on which a computer program that allows a computer to execute an information processing method is recorded, the information processing method comprising:

storing first identification information for indicating a person related to a newborn in a storage unit;

acquiring first newborn living-body information from the newborn;

determining which one of predetermined plurality types of pattern is a type of pattern that the first newborn living-body information has; and causing the storage unit to store first determination information indicating a determination result in association with the first identification information, wherein the information processing method further comprises:

acquiring at least two pieces of the first newborn living-body information from the newborn;

for each of the at least two pieces of the first newborn living-body information, determining which one of the plurality types of pattern is the type of pattern that the first newborn living-body information has; and causing the storage unit to store in association with the first identification information, the first determination information in which the determination result corresponding to each of the at least two pieces of the first newborn living-body information is combined with each other.

* * * * *